(12) United States Patent
Rowe et al.

(10) Patent No.: US 7,708,775 B2
(45) Date of Patent: May 4, 2010

(54) METHODS FOR RAPID DEPLOYMENT OF PROSTHETIC HEART VALVES

(75) Inventors: Stanton J. Rowe, Newport Beach, CA (US); Larry Wood, Rancho Santa Margarita, CA (US); Henry Bourang, Irvine, CA (US); George Bakis, La Habra Heights, CA (US); Benjamin Spenser, Caesarea (IL); Netanel Benichou, Nir-Etzion (IL); Yaron Keidar, Haifa (IL); Assaf Bash, Givat Ada (IL)

(73) Assignee: Edwards Lifesciences Corporation, Irvine, CA (US)

( * ) Notice: Subject to any disclaimer, the term of this patent is extended or adjusted under 35 U.S.C. 154(b) by 464 days.

(21) Appl. No.: 11/441,405

(22) Filed: May 24, 2006

(65) Prior Publication Data

US 2006/0287717 A1 Dec. 21, 2006

Related U.S. Application Data

(60) Provisional application No. 60/684,443, filed on May 24, 2005.

(51) Int. Cl.
*A61F 2/24* (2006.01)
(52) U.S. Cl. ................................... 623/2.11
(58) Field of Classification Search ............... 623/1.11, 623/2.1–2.42
See application file for complete search history.

(56) References Cited

U.S. PATENT DOCUMENTS

| | | | |
|---|---|---|---|
| 3,143,742 A | 8/1964 | Cromie | |
| 3,371,352 A | 3/1968 | Siposs et al. | |
| 3,546,710 A | 12/1970 | Shumakov Valery Ivanovich at al. | |
| 3,574,865 A | 4/1971 | Hamaker | |
| 3,839,741 A | 10/1974 | Haller | |
| 3,997,923 A | 12/1976 | Possis | |
| 4,106,129 A * | 8/1978 | Carpentier et al. | 623/2.18 |
| 4,211,325 A * | 7/1980 | Wright | 206/438 |

(Continued)

FOREIGN PATENT DOCUMENTS

EP 1171059 1/2002

(Continued)

*Primary Examiner*—(Jackie) Tan-Uyen T. Ho
*Assistant Examiner*—Son Dang
(74) *Attorney, Agent, or Firm*—Rajiv Yadav, Esq.; Guy Cumberbatch, Esq.

(57) ABSTRACT

A two-stage or component-based valve prosthesis that can be quickly and easily implanted during a surgical procedure is provided. The prosthetic valve comprises a support structure that is deployed at a treatment site. The prosthetic valve further comprises a valve member configured to be quickly connected to the support structure. The support structure may take the form of a stent that is expanded at the site of a native valve. If desired, the native leaflets may remain and the stent may be used to hold the native valve open. In this case, the stent may be balloon expandable and configured to resist the powerful recoil force of the native leaflets. The support structure is provided with a coupling means for attachment to the valve member, thereby fixing the position of the valve member in the body. The valve member may be a non-expandable type, or may be expandable from a compressed state to an expanded state. The system is particularly suited for rapid deployment of heart valves in a conventional open-heart surgical environment.

22 Claims, 26 Drawing Sheets

U.S. PATENT DOCUMENTS

| | | | |
|---|---|---|---|
| 4,217,665 A | 8/1980 | Bex | |
| 4,470,157 A * | 9/1984 | Love | 623/2.15 |
| 4,680,031 A | 7/1987 | Alonso | |
| 4,705,516 A | 11/1987 | Barone et al. | |
| 4,790,843 A | 12/1988 | Carpentier et al. | |
| 4,960,424 A | 10/1990 | Grooters | |
| 5,032,128 A | 7/1991 | Alonso | |
| 5,163,953 A * | 11/1992 | Vince | 623/2.11 |
| 5,332,402 A | 7/1994 | Teitelbaum | |
| 5,397,351 A | 3/1995 | Pavcnik et al. | |
| 5,431,676 A | 7/1995 | Dubrul et al. | |
| 5,571,215 A | 11/1996 | Sterman et al. | |
| 5,578,076 A | 11/1996 | Krueger et al. | |
| 5,584,803 A | 12/1996 | Stevens et al. | |
| 5,618,307 A | 4/1997 | Donlon et al. | |
| 5,626,607 A | 5/1997 | Malecki et al. | |
| 5,628,789 A | 5/1997 | Vanney et al. | |
| 5,693,090 A | 12/1997 | Unsworth et al. | |
| 5,695,503 A | 12/1997 | Krueger et al. | |
| 5,713,952 A | 2/1998 | Vanney et al. | |
| 5,716,370 A * | 2/1998 | Williamson et al. | 606/153 |
| 5,728,151 A | 3/1998 | Garrison et al. | |
| 5,735,894 A | 4/1998 | Krueger et al. | |
| 5,814,097 A | 9/1998 | Sterman et al. | |
| 5,824,064 A | 10/1998 | Taheri | |
| 5,840,081 A | 11/1998 | Andersen et al. | |
| 5,855,601 A | 1/1999 | Bessler et al. | |
| 5,908,450 A | 6/1999 | Gross et al. | |
| 5,957,949 A | 9/1999 | Leonhardt et al. | |
| 5,984,959 A | 11/1999 | Robertson et al. | |
| 5,984,973 A | 11/1999 | Girard et al. | |
| 6,010,531 A | 1/2000 | Donlon et al. | |
| 6,042,607 A | 3/2000 | Williamson, IV et al. | |
| 6,066,160 A | 5/2000 | Colvin et al. | |
| 6,074,418 A | 6/2000 | Buchanan et al. | |
| 6,106,550 A | 8/2000 | Magovern et al. | |
| 6,162,233 A | 12/2000 | Williamson, IV et al. | |
| 6,168,614 B1 | 1/2001 | Andersen et al. | |
| 6,176,877 B1 | 1/2001 | Buchanan et al. | |
| 6,197,054 B1 | 3/2001 | Hamblin, Jr. et al. | |
| 6,217,611 B1 | 4/2001 | Klostermeyer | |
| 6,231,561 B1 | 5/2001 | Frazier et al. | |
| 6,241,765 B1 | 6/2001 | Griffin et al. | |
| 6,245,102 B1 | 6/2001 | Jayaraman | |
| 6,264,691 B1 * | 7/2001 | Gabbay | 623/2.14 |
| 6,283,127 B1 | 9/2001 | Sterman et al. | |
| 6,287,339 B1 | 9/2001 | Vazquez et al. | |
| 6,290,674 B1 | 9/2001 | Roue et al. | |
| 6,312,447 B1 | 11/2001 | Grimes | |
| 6,312,465 B1 | 11/2001 | Griffin et al. | |
| 6,328,727 B1 | 12/2001 | Frazier et al. | |
| 6,402,780 B2 | 6/2002 | Williamson | |
| 6,425,916 B1 * | 7/2002 | Garrison et al. | 623/2.11 |
| 6,440,164 B1 | 8/2002 | DiMatteo et al. | |
| 6,454,799 B1 * | 9/2002 | Schreck | 623/2.18 |
| 6,458,153 B1 | 10/2002 | Bailey et al. | |
| 6,468,305 B1 | 10/2002 | Otte | |
| 6,582,462 B1 | 6/2003 | Andersen et al. | |
| 6,652,578 B2 | 11/2003 | Bailey et al. | |
| 6,685,739 B2 | 2/2004 | DiMatteo et al. | |
| 6,730,118 B2 | 5/2004 | Spenser et al. | |
| 6,733,525 B2 * | 5/2004 | Yang et al. | 623/2.18 |
| 6,764,508 B1 | 7/2004 | Roehe et al. | |
| 6,767,362 B2 * | 7/2004 | Schreck | 623/2.11 |
| 6,786,925 B1 | 9/2004 | Schoon et al. | |
| 6,790,229 B1 | 9/2004 | Berreklouw | |
| 6,790,230 B2 | 9/2004 | Beyersdorf et al. | |
| 6,805,711 B2 | 10/2004 | Quijano et al. | |
| 6,893,459 B1 | 5/2005 | Macoviak | |
| 6,893,460 B2 | 5/2005 | Spenser et al. | |
| 6,908,481 B2 | 6/2005 | Cribier | |
| 6,939,365 B1 | 9/2005 | Fogarty et al. | |
| 7,011,681 B2 | 3/2006 | Vesely | |
| 7,025,780 B2 | 4/2006 | Gabbay | |
| 7,070,616 B2 | 7/2006 | Majercak et al. | |
| 7,097,659 B2 | 8/2006 | Woolfson et al. | |
| 7,101,396 B2 | 9/2006 | Artof et al. | |
| 7,147,663 B1 * | 12/2006 | Berg et al. | 623/2.38 |
| 7,153,324 B2 | 12/2006 | Case et al. | |
| 7,195,641 B2 | 3/2007 | Palmaz et al. | |
| 7,201,772 B2 | 4/2007 | Schwammenthal et al. | |
| 7,252,682 B2 | 8/2007 | Seguin | |
| 7,261,732 B2 | 8/2007 | Justino | |
| 7,393,360 B2 * | 7/2008 | Spenser et al. | 623/2.18 |
| 2001/0007956 A1 * | 7/2001 | Letac et al. | 623/2.11 |
| 2001/0021872 A1 * | 9/2001 | Bailey et al. | 623/1.24 |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0049492 A1 | 12/2001 | Frazier et al. | |
| 2002/0026238 A1 | 2/2002 | Lane et al. | |
| 2002/0032481 A1 * | 3/2002 | Gabbay | 623/2.11 |
| 2002/0058995 A1 | 5/2002 | Stevens | |
| 2002/0077698 A1 * | 6/2002 | Peredo | 623/2.13 |
| 2002/0123802 A1 | 9/2002 | Snyders | |
| 2002/0138138 A1 | 9/2002 | Yang | |
| 2002/0188348 A1 | 12/2002 | DiMatteo et al. | |
| 2002/0198594 A1 * | 12/2002 | Schreck | 623/2.11 |
| 2003/0014104 A1 * | 1/2003 | Cribier | 623/2.11 |
| 2003/0023300 A1 | 1/2003 | Bailey et al. | |
| 2003/0023303 A1 | 1/2003 | Palmaz et al. | |
| 2003/0036795 A1 | 2/2003 | Andersen et al. | |
| 2003/0040792 A1 | 2/2003 | Gabbay | |
| 2003/0055495 A1 | 3/2003 | Pease et al. | |
| 2003/0109924 A1 | 6/2003 | Cribier | |
| 2003/0114913 A1 * | 6/2003 | Spenser et al. | 623/1.11 |
| 2003/0130729 A1 | 7/2003 | Paniagua et al. | |
| 2003/0149477 A1 | 8/2003 | Gabbay | |
| 2003/0149478 A1 | 8/2003 | Figulla et al. | |
| 2003/0153974 A1 | 8/2003 | Spenser et al. | |
| 2003/0167089 A1 | 9/2003 | Lane | |
| 2003/0236568 A1 | 12/2003 | Hojeibane et al. | |
| 2004/0019374 A1 | 1/2004 | Hojeibane et al. | |
| 2004/0034411 A1 | 2/2004 | Quijano et al. | |
| 2004/0039436 A1 | 2/2004 | Spenser et al. | |
| 2004/0044406 A1 | 3/2004 | Woolfson et al. | |
| 2004/0093075 A1 | 5/2004 | Kuehne | |
| 2004/0106976 A1 | 6/2004 | Bailey et al. | |
| 2004/0122514 A1 | 6/2004 | Fogarty et al. | |
| 2004/0122516 A1 | 6/2004 | Fogarty et al. | |
| 2004/0122526 A1 | 6/2004 | Imran | |
| 2004/0186563 A1 | 9/2004 | Lobbi | |
| 2004/0186565 A1 | 9/2004 | Schreck | |
| 2004/0193261 A1 | 9/2004 | Berreklouw | |
| 2004/0206363 A1 | 10/2004 | McCarthy et al. | |
| 2004/0210304 A1 | 10/2004 | Seguin et al. | |
| 2004/0210307 A1 | 10/2004 | Khairkhahan | |
| 2004/0225355 A1 | 11/2004 | Stevens | |
| 2004/0236411 A1 | 11/2004 | Sarac et al. | |
| 2004/0260389 A1 | 12/2004 | Case et al. | |
| 2004/0260390 A1 | 12/2004 | Sarac et al. | |
| 2005/0010285 A1 | 1/2005 | Lambrecht et al. | |
| 2005/0027348 A1 | 2/2005 | Case et al. | |
| 2005/0033398 A1 | 2/2005 | Seguin | |
| 2005/0043760 A1 | 2/2005 | Fogarty et al. | |
| 2005/0043790 A1 | 2/2005 | Seguin | |
| 2005/0060029 A1 | 3/2005 | Le et al. | |
| 2005/0065594 A1 | 3/2005 | DiMatteo et al. | |
| 2005/0065614 A1 | 3/2005 | Stinson | |
| 2005/0075584 A1 | 4/2005 | Cali | |
| 2005/0075713 A1 | 4/2005 | Biancucci et al. | |
| 2005/0075717 A1 | 4/2005 | Nguyen et al. | |
| 2005/0075718 A1 | 4/2005 | Nguyen et al. | |

| | | |
|---|---|---|
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 * | 6/2005 | Salahieh et al. ............ 623/2.11 |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 * | 4/2006 | Campbell .................. 623/1.26 |
| 2006/0095125 A1 | 5/2006 | Chinn et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0270944 A1 | 11/2007 | Bergheim et al. |
| 2008/0281411 A1 * | 11/2008 | Berreklouw ............... 623/2.11 |

FOREIGN PATENT DOCUMENTS

| | | |
|---|---|---|
| GB | 2254254 | 10/1992 |
| WO | WO 97/09933 | 9/1995 |
| WO | WO 97/09944 | 9/1995 |
| WO | WO 97/27799 | 1/1997 |
| WO | WO 99/15112 | 9/1997 |
| WO | WO 00/60995 | 4/1999 |
| WO | WO 2006/086135 | 8/2006 |

* cited by examiner

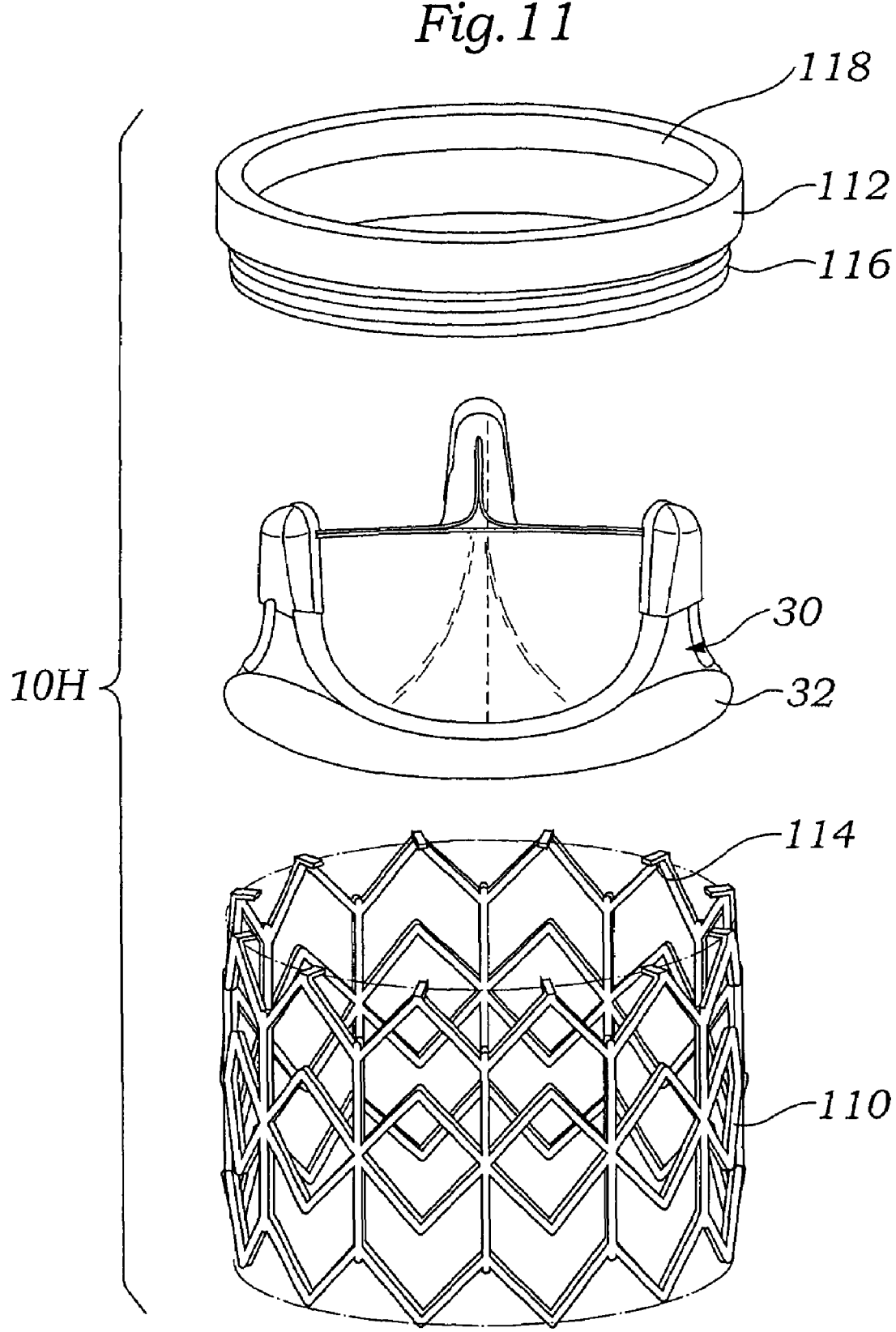

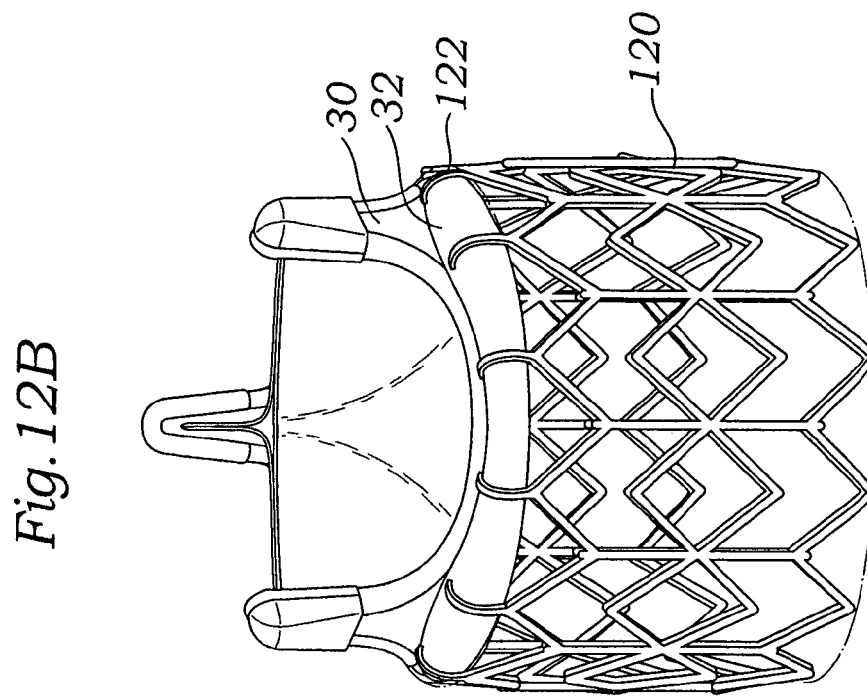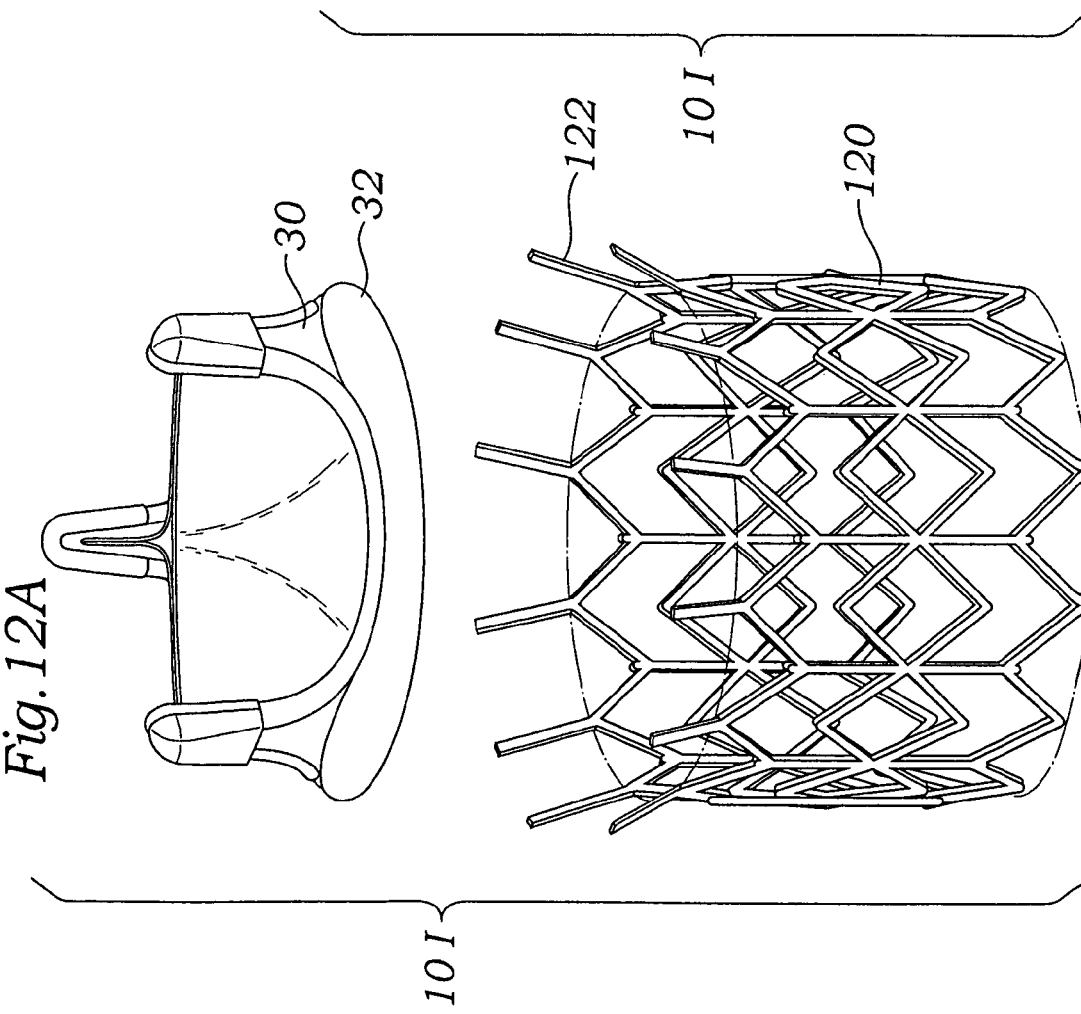

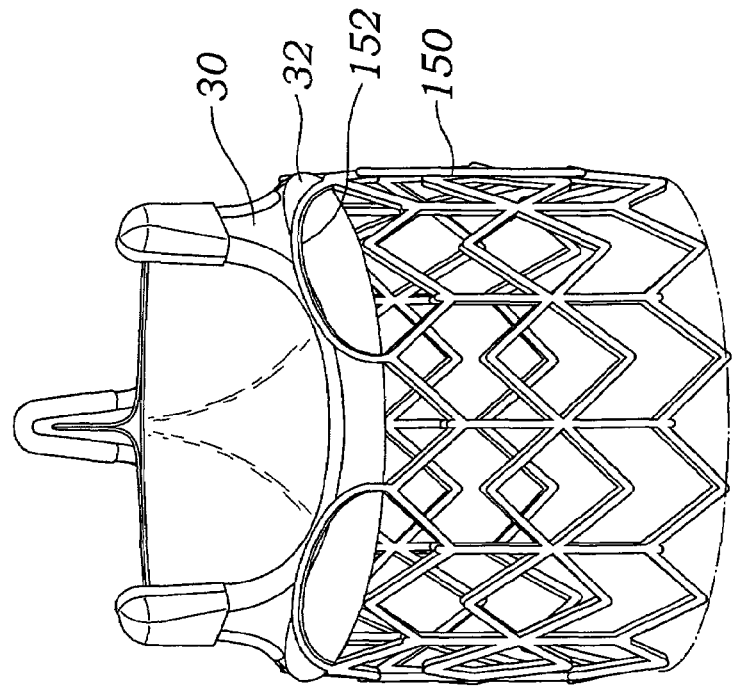
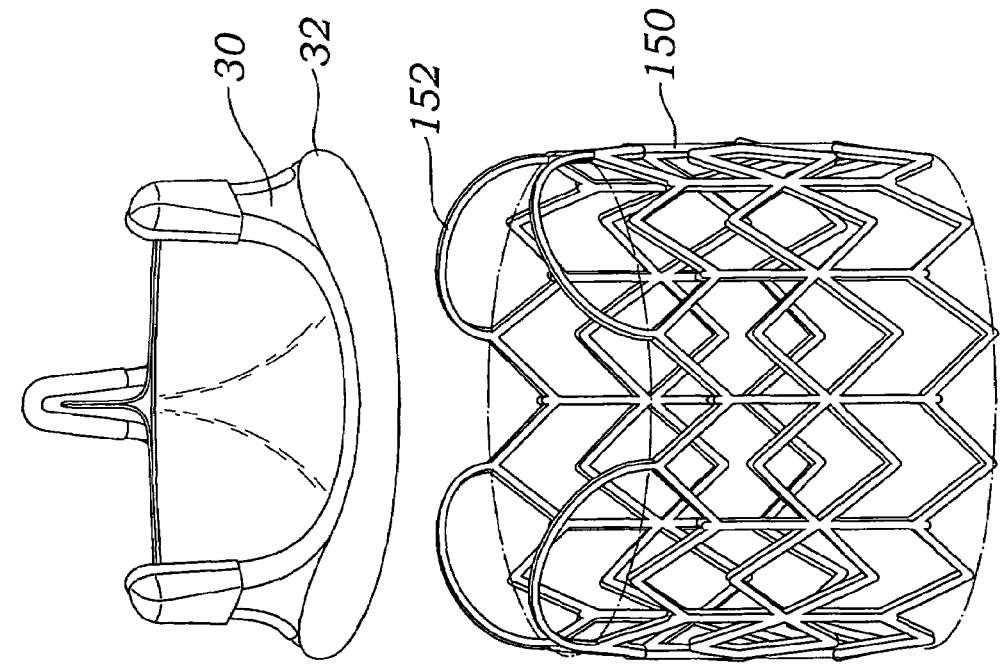
Fig.15A
Fig.15B

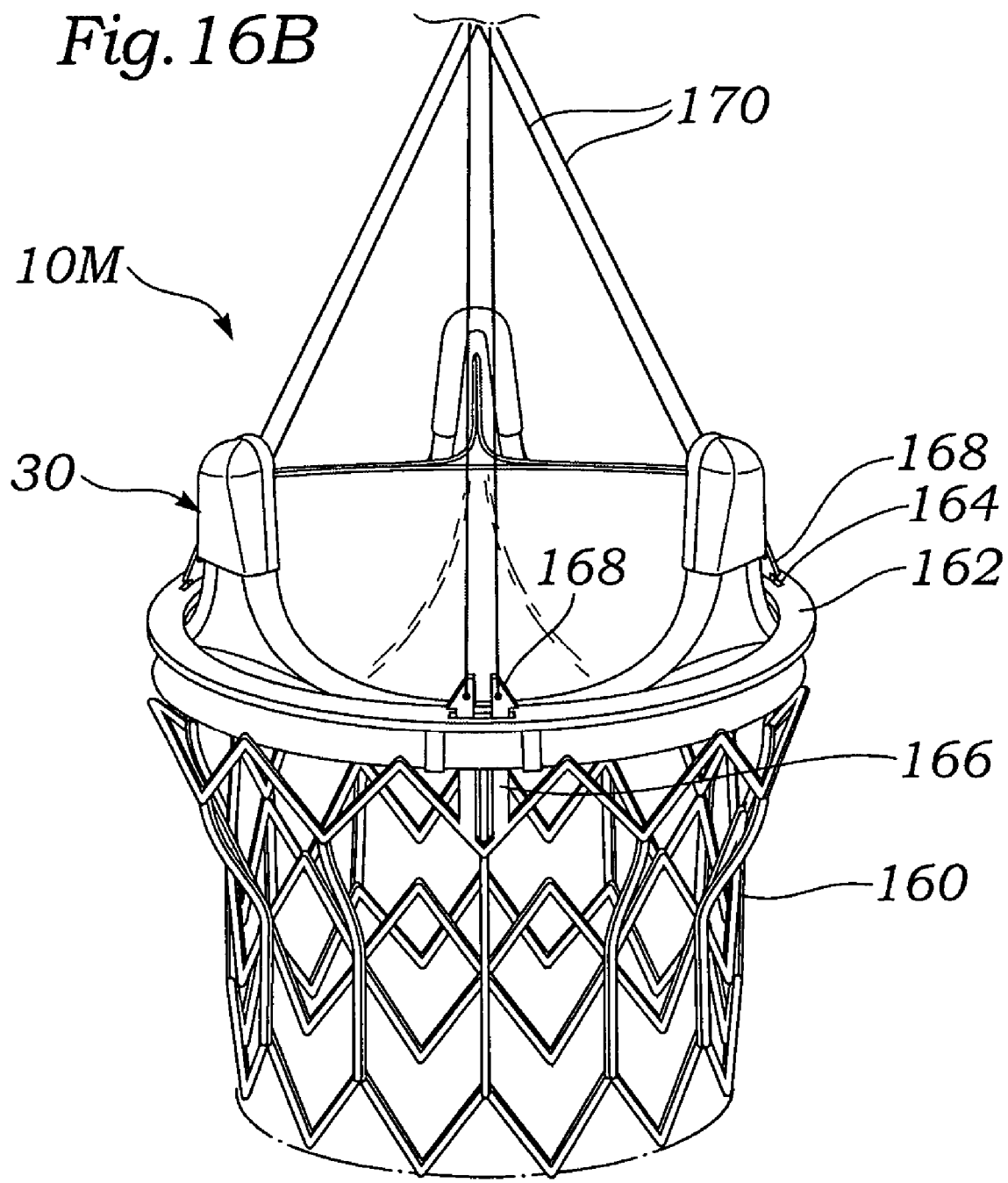

METHODS FOR RAPID DEPLOYMENT OF PROSTHETIC HEART VALVES

RELATED APPLICATIONS

The present invention claims priority to Provisional Application No. 60/684,443, filed on May 24, 2005, entitled "Prosthetic Valve for Implantation in a Body Channel."

FIELD OF THE INVENTION

The present invention generally relates to prosthetic valves for implantation in body channels. More particularly, the present invention relates to prosthetic heart valves configured to be surgically implanted in less time than current valves.

BACKGROUND OF THE INVENTION

Due to aortic stenosis and other heart valve diseases, thousands of patients undergo surgery each year wherein the defective native heart valve is replaced by a prosthetic valve, either bioprosthetic or mechanical. When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new regimens of heart valve replacement, regulatory bodies around the world are moving slowly as well. Numerous successful clinical trials and follow-up studies are in process, but much more experience with these new technologies will be required before they are completely accepted. One question that remains unanswered is whether the new expandable valves will have the same durability as conventional prosthetic heart valves.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure. The present invention addresses this need.

SUMMARY OF THE INVENTION

Various embodiments of the present invention provide prosthetic valves and methods of use for replacing a defective native valve in a human heart. Certain embodiments are particularly well adapted for use in a surgical procedure for quickly and easily replacing a heart valve while minimizing time using extracorporeal circulation (i.e., bypass pump).

In one embodiment, a method for treating a native aortic valve in a human heart, comprises: 1) accessing a native valve through an opening in a chest; 2) advancing an expandable support structure to the site of a native aortic valve, the support structure being radially compressed during the advancement; 3) radially expanding the support structure at the site of the native aortic valve; and 4) mechanically coupling a valve member to the expanded support structure, wherein the valve member replaces the function of the native aortic valve. A further understanding of the nature and advantages of the present invention are set forth in the following description and claims, particularly when considered in conjunction with the accompanying drawings in which like parts bear like reference numerals.

In one variation, the support structure is a stent, which may comprise a metallic frame. In one embodiment, at least a portion of the metallic frame is made of stainless steel. In another embodiment, at least a portion of the metallic frame is made of a shape memory material. The valve member may take a variety of forms. In one preferred embodiment, the valve member comprises biological tissue. The valve member further comprises a coupling portion configured to be connected to the support structure in a quick and efficient manner. In another variation of this method, the metallic frame is viewed under fluoroscopy during advancement of the prosthetic valve toward the native aortic valve.

The native valve leaflets may be removed before delivering the prosthetic valve. Alternatively, the native leaflets may be left in place to reduce surgery time and to provide a stable base for fixing the support structure within the native valve. In one advantage of this method, the native leaflets recoil inward to enhance the fixation of the metallic frame in the body channel. When the native leaflets are left in place, a balloon or other expansion member may be used to push the valve leaflets out of the way and thereby dilate the native valve before implantation of the support structure.

In another preferred embodiment, a method for treating a native aortic valve in a human heart, comprises accessing a native valve through an opening in a chest; advancing an expandable member to a position within the native aortic valve, the native aortic valve having at least two valvular leaflets; dilating the native aortic valve by expanding the expandable member to push aside the valvular leaflets of the native aortic valve; collapsing the expandable member and withdrawing the expandable member from the native aortic valve; advancing an expandable support structure to a position within the dilated native aortic valve, the support structure being radially compressed during the advancement; radially expanding the support structure within the dilated aortic valve, wherein the expanded support structure maintains the native aortic valve in the dilated condition; and coupling a valve member to the expanded support structure, wherein the valve member replaces the function of the native aortic valve.

In another aspect, an improved prosthetic valve comprises an expandable stent sized for implantation at the site of a native aortic valve, the stent having a coupling means (e.g., a plurality of tines extending from a first end thereof); and a valve member comprising three leaflets mounted on a base portion. The coupling means is configured for attachment to the valve member. Alternatively, the coupling means may be provided on the valve member or on both the stent and valve member.

A particularly useful configuration of the present invention is a two-stage prosthetic heart valve, comprising an expandable anchoring member sized to contact a heart valve annulus in an expanded state and a substantially non-expandable valve member configured for connection to the anchoring member. Desirably, the valve member includes a base ring surrounding an inflow end thereof, and the anchoring member comprises a tubular structure having connectors adapted to engage the base ring. The connectors may comprise prongs that change shape and engage the base ring. For example, the base ring may be made of a suture-permeable material, and the prongs are configured to pierce the base ring, or the prongs are shaped to wrap around the base ring.

In an exemplary embodiment, the valve member includes a plurality of discrete connectors spaced around a peripheral inflow end thereof, and the anchoring member comprises a tubular structure having a plurality of mating connectors spaced around a peripheral outflow end thereof. The connectors on the valve member and anchoring member engage one another by displacing the valve member toward the anchoring member. For instance, the connectors on either the valve member or anchoring member comprise latches, and the connectors on the other of the valve member or anchoring member comprise brackets, the latches configured to engage and lock to the brackets upon axial movement of the latches and brackets toward one another. Additionally, a plurality of guide filaments may be provided, at least one for each of the connectors on the anchoring member and slidingly received by the associated connector on the valve member. The guide filaments guide the valve member in proper orientation with respect to the anchoring member to ensure engagement of the mating connectors.

Desirably, the anchoring member comprises a stent having a wider outflow end than an inflow end thereof, wherein the valve member comprises a base ring surrounding an inflow end thereof that fits within the outflow end of the stent. In one embodiment, the valve member includes a suture-permeable base ring surrounding an inflow end thereof, and the anchoring member comprises a tubular structure having a suture-permeable fixation ring attached thereto, wherein the valve member connects to the anchoring member via sutures looped between the base ring and the fixation ring.

Another embodiment of the present invention comprises a two-stage prosthetic heart valve, having an expandable anchoring member sized to contact a heart valve annulus in an expanded state, a valve member, and an adapter sized to surround the valve member and engage the anchoring member, to connect the valve member and anchoring member. The adapter may be an annular ring or a wireform-shaped member that closely surrounds and conforms to cusps and commissures of a flexible leaflet valve member.

Whatever its shape, the adapter desirably includes a plurality of discrete connectors, and the anchoring member comprises a tubular structure having a plurality of mating connectors spaced around a peripheral outflow end thereof. The connectors on the adapter and anchoring member are configured to engage one another by displacing the adapter toward the anchoring member. For example, the connectors on either the adapter or anchoring member comprise latches, and the connectors on the other of the adapter or anchoring member comprise brackets, the latches being configured to engage and lock to the brackets upon axial movement of the latches and brackets toward one another. In addition, the valve member preferably has a base ring surrounding an inflow end thereof, and the adapter further includes a plurality of connectors adapted to engage and couple the adapter directly to the base ring.

Another aspect of the present invention is a system for retrofitting a conventional prosthetic heart valve, comprising an off-the-shelf, non-expandable prosthetic heart valve having a sewing ring capable of being implanted using sutures through the sewing ring in an open-heart procedure. An expandable anchoring member contacts and anchors to a heart valve annulus in an expanded state. Coupling means connects the prosthetic heart valve to the anchoring member, the prosthetic heart valve thus being attached to the heart valve annulus via the anchoring member.

In the system for retrofitting a conventional prosthetic heart valve, the anchoring member may comprise a tubular structure having a suture-permeable fixation ring attached thereto, wherein the coupling means comprises sutures looped between the base ring and the fixation ring. An adapter sized to surround the heart valve engages the anchoring member, to connect the heart valve and anchoring member. The adapter may be annular or wireform-shaped. Desirably, the adapter includes a plurality of discrete connectors, and the anchoring member comprises a tubular structure having a plurality of mating connectors spaced around a peripheral outflow end thereof, the connectors on the adapter and anchoring member being configured to engage one another by displacing the adapter toward the anchoring member.

A surgical method of implanting a prosthetic heart valve of the present invention in a patient involves providing a two-stage prosthetic heart valve comprising an expandable anchoring member and a valve member, the anchoring member being sized to contact a heart valve annulus in an expanded state and the valve member being configured to connect to the anchoring member. The patient is prepared for surgery by placing him/her on cardiopulmonary bypass. The surgeon creates a direct access pathway to the heart valve annulus that preferably permits direct (i.e., naked eye) visualization of the heart valve annulus. The anchoring member is delivered and expanded to contact the valve annulus, and the valve member is delivered and connected to the anchoring member. Preferably, the direct access pathway is created by performing open-heart surgery. The method may include balloon-expanding the anchoring member. Further, the valve member may be expandable and the method includes delivering the valve member in a compressed state and expanding it prior to connecting it to the anchoring member.

In one embodiment, the valve member and the anchoring member are provided with mating connectors, and the step of delivering and connecting the valve member to the anchoring member comprises axially displacing the valve member toward the anchoring member so that the mating connectors engage. In another embodiment, the anchoring member comprises a stent having an outflow end larger than an inflow end thereof, and the valve member comprises a non-expandable valve member having a base ring on an inflow end thereof sized to fit within the outflow end of the stent. The anchoring member may be provided with bendable connectors on an outflow end thereof, and the method includes causing the connectors to bend inward and engage a peripheral base ring of the valve member. For example, a bending tool may be used to bend connectors inward.

Another surgical method of implanting a two-stage prosthetic heart valve in a patient of the present invention includes providing an expandable anchoring member sized to contact a heart valve annulus in an expanded state, delivering and attaching the anchoring member to the heart valve annulus, providing a non-expandable valve member, and delivering and connecting the valve member to the anchoring member. The valve member and the anchoring member may be provided with mating connectors, and the step of delivering and connecting the valve member to the anchoring member comprises axially displacing the valve member toward the anchoring member so that the mating connectors engage. Desirably, the anchoring member comprises a stent having an outflow end larger than an inflow end thereof, and wherein the valve member comprises a base ring on an inflow end thereof sized to fit within the outflow end of the stent. The anchoring member may be provided with bendable connectors on an outflow end thereof, and the method includes causing the connectors to bend inward and engage a peripheral base ring of the valve member, such as by using a bending tool.

In an exemplary embodiment, the valve member includes a base ring on an inflow end thereof, and the method further includes providing an adapter sized to surround the valve member and seat on the base ring. The method therefore includes the step of delivering and connecting the valve member and coupling the adapter to the anchoring member. For instance, the adapter includes a plurality of discrete connectors, and the anchoring member comprises a tubular structure having a plurality of mating connectors spaced around a peripheral outflow end thereof. The step of coupling the adapter to the anchoring member comprises displacing the adapter toward the anchoring member to engage the mating connectors thereon. Additionally, the adapter may further have a plurality of connectors adapted to engage and couple the adapter directly to the base ring, and the method includes causing the connectors to engage the base ring.

In a still further surgical method of implanting a prosthetic heart valve in a patient, a prosthetic heart valve and a separate expandable anchoring member are provided. The prosthetic heart valve and anchoring member are positioned within a valve dilator/delivery tube having an exterior diameter sized to dilate a heart valve annulus. The valve dilator/delivery tube advances to the heart valve annulus, and the annulus is dilated using the valve dilator/delivery tube. The anchoring member is expulsed from the tube and expanded to contact the heart valve annulus. The prosthetic heart valve is then expulsed from the valve dilator/delivery tube, and connected to the anchoring member.

Another method of the present invention comprises retrofitting and rapidly implanting a conventional prosthetic heart valve in a patient. The method includes providing an off-the-shelf non-expandable prosthetic heart valve having a sewing ring capable of being implanted using sutures through the sewing ring in an open-heart procedure. An expandable tissue anchoring member sized to contact a heart valve annulus in an expanded state is delivered and expanded into contact with the heart valve annulus. Finally, the prosthetic heart valve is delivered and connected to the tissue anchoring member.

BRIEF DESCRIPTION OF THE DRAWINGS

The invention will now be explained and other advantages and features will appear with reference to the accompanying schematical drawings wherein:

FIG. 11 is an exploded perspective view of an alternative prosthetic heart valve of the present invention having a valve member, stent, and a threaded locking ring for coupling the two together.

FIGS. 12A and 12B are exploded and assembled perspective views of an alternative two-stage prosthetic heart valve having a valve member and tubular, expandable stent with tabs on an outflow end for coupling to the valve member.

FIGS. 15A and 15B are exploded and assembled perspective views of a prosthetic heart valve having a valve member and stent with locking bands on an outflow end.

FIGS. 16A and 16B are exploded and assembled perspective views of an alternative prosthetic heart valve wherein a stent exhibits locking clips on an outflow end that are guided through mating slits on a locking ring to join the stent to a valve member.

DETAILED DESCRIPTION OF THE PREFERRED EMBODIMENTS

Figure 1:
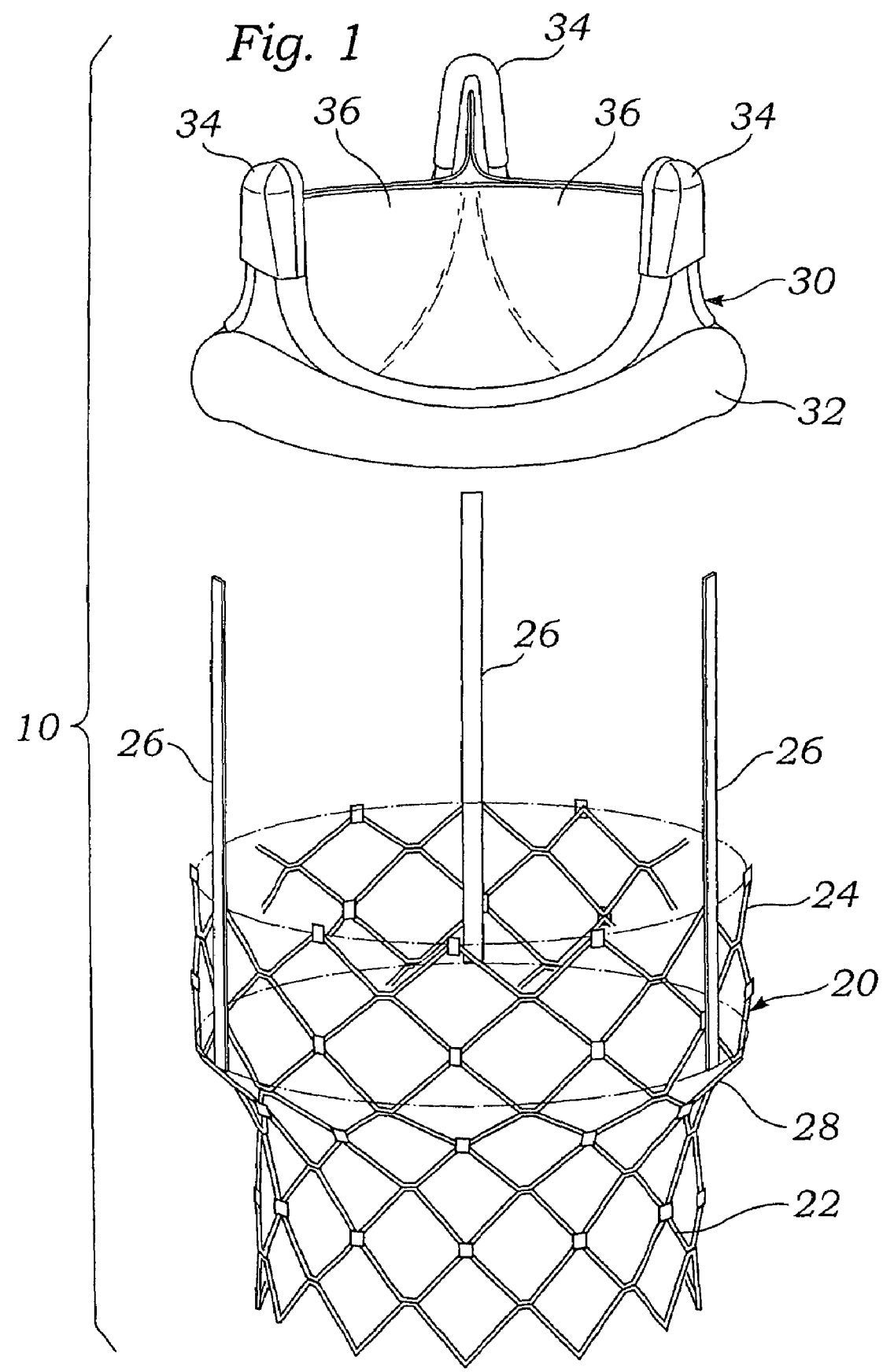
FIG. 1 is an exploded perspective view illustrating a preferred embodiment of a two-stage prosthetic valve comprising a stent portion and a valve member, wherein the valve member may be quickly and easily connected to the stent portion.

The present invention attempts to overcome drawbacks associated with conventional, open-heart surgery, while also adopting some of the techniques of newer technologies which decrease the duration of the treatment procedure. The prosthetic heart valves of the present invention are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the two-stage prosthetic heart valves described herein may also be configured for delivery using percutaneous approaches, and those minimally-invasive surgical approaches that require remote implantation of the valve using indirect visualization.

One primary aspect of the present invention is a two-stage prosthetic heart valve wherein the tasks of implanting a tissue anchor and a valve member are somewhat separated and certain advantages result. For example, a two-stage prosthetic heart valve of the present invention may have an expandable tissue anchoring member that is secured in the appropriate location using a balloon or other expansion technique. A valve member is then coupled to the tissue anchoring member in a separate or sequential operation. By utilizing an expandable anchoring member, the duration of the initial anchoring operation is greatly reduced as compared with a conventional sewing procedure utilizing an array of sutures. The expandable anchoring member may simply be radially expanded outward into contact with the implantation site, or may be provided with additional anchoring means, such as barbs. The operation may be carried out using a conventional open-heart approach and cardiopulmonary bypass. In one advantageous feature, the time on bypass is greatly reduced due to the relative speed of implanting the expandable anchoring member.

For definitional purposes, the term "tissue anchoring member," or simply "anchoring member" refers to a structural component of a heart valve that is capable of attaching to tissue of a heart valve annulus. The anchoring members described herein are most typically tubular stents, or stents having varying diameters. A stent is normally formed of a biocompatible metal wire frame, such as stainless steel or Nitinol. Other anchoring members that could be used with valves of the present invention include rigid rings, spirally-wound tubes, and other such tubes that fit tightly within a valve annulus and define an orifice therethrough for the passage of blood, or within which a valve member is mounted. It is entirely conceivable, however, that the anchoring member could be separate clamps or hooks that do not define a continuous periphery. Although such devices sacrifice some dynamic stability, these devices can be configured to work well in conjunction with a particular valve member.

The term "valve member" refers to that component of a heart valve that possesses the fluid occluding surfaces to prevent blood flow in one direction while permitting it in another. As mentioned above, various constructions of valve numbers are available, including those with flexible leaflets and those with rigid leaflets or a ball and cage arrangement. The leaflets may be bioprosthetic, synthetic, or metallic.

A primary focus of the present invention is the two-stage prosthetic heart valve having a first stage in which an anchoring member secures to a valve annulus, and a subsequent second stage in which a valve member connects to the anchoring member. It should be noted that these stages can be done almost simultaneously, such as if the two components were mounted on the same delivery device, or can be done in two separate clinical steps, with the anchoring member deployed using a first delivery device, and then the valve member using another delivery device. It should also be noted that the term "two-stage" does not necessarily limit the valve to just two parts, as will be seen below.

Another potential benefit of a two-stage prosthetic heart valve, including an anchoring member and a valve member, is that the valve member may be replaced after implantation without replacing the anchoring member. That is, an easily detachable means for coupling the valve member and anchoring member may be used that permits a new valve member to be implanted with relative ease. Various configurations for coupling the valve member and anchoring member are described herein.

It should be understood, therefore, that certain benefits of the invention are independent of whether the anchoring member or valve member are expandable or not. That is, various embodiments illustrate an expandable anchoring member coupled to a conventional valve member. However, the same coupling structure may be utilized for a non-expandable anchoring member and conventional valve member. Additionally, although a primary embodiment of the present invention is an expandable anchoring member coupled with a conventional valve member, both could be expandable and introduced percutaneously or through a minimally-invasive approach. Therefore, the invention should not be construed as being limited in these regards, but instead should be interpreted via the appended claims.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other. However, unless the combination is structurally impossible, or excluded by claim language, any of the heart valve embodiments described herein could be implanted in any body channel.

With reference now to FIG. 1, one preferred embodiment of an improved prosthetic valve 10 generally includes an expandable anchoring member or stent 20 and a valve member 30. The stent provides a support structure for anchoring the valve member within a body lumen. Although a stent is described for purposes of illustration, any support structure capable of anchoring the valve member to the body lumen may be used. As will be described in more detail below, the prosthetic valve is configured such that the valve member may be quickly and easily connected to the stent. It should be noted here, that the anchoring members or stents described herein can be a variety of designs, including having the diamond-shaped openings shown or other configurations detailed below. The material depends on the mode of delivery (i.e., balloon- or self-expanding), and the stent can be bare strut material or covered to promote ingrowth and/or to reduce paravalvular leakage. For example, a suitable cover that is often used is a sleeve of fabric such as Dacron.

The stent may be securely deployed in the body channel using an expandable member, such as, for example, a balloon. Because the stent is expanded before the valve member is attached, the valve member will not be damaged or otherwise adversely affected during the stent deployment. After the stent has been deployed in the body channel, the valve member may be connected to the stent. In one preferred application, the two-stage prosthetic valve is well-suited for use in heart valve replacement. In this application, the stent may be advantageously used to push the native leaflets aside such that the valve member can replace the function of the native valve. The anchoring members or stents described herein could include barbs or other such tissue anchors to further secure the stent to the tissue. In one preferred embodiment, the barbs are deployable (e.g., configured to extend or be pushed radially outward) by the expansion of a balloon.

In another advantageous feature, the two-stage prosthetic valve illustrated in FIG. 1 provides a device and method for substantially reducing the time of the surgical procedure. This reduces the time required on extracorporeal circulation and thereby substantially reduces the risk to the patient. The surgical time is reduced because the stent may be deployed quickly and the valve member may be attached to the stent quickly. This simplifies and reduces the surgical time as compared with replacement valves that are sutured to the tissue after removing the native leaflets.

When used for aortic valve replacement, the valve member 30 preferably has three leaflets 36 which provide the valvular function for replacing the function of the native valve. In various preferred embodiments, the valve leaflets may be taken from another human heart (cadaver), a cow (bovine), a pig (porcine valve) or a horse (equine). In other preferred variations, the valve member may comprise mechanical components rather than biological tissue. In one preferred embodiment, the valve is compressible in diameter. Accordingly, the valve may be reduced in diameter for delivery into the stent and then expanded. The three leaflets are supported by three commissural posts 34. A ring 32 is provided along the base portion of the valve member.

With continued reference to FIG. 1, the stent 20 is provided with two diameters. A lower portion 22 has a small diameter and an upper portion 24 has a large diameter. The lower portion 22 is preferably sized to be deployed at the location of the native valve (e.g., along the aortic annulus). The upper portion 24 expands outwardly into the perspective cavity adjacent the native valve. For example, in an aortic valve replacement, the upper portion 24 expands into the area of the sinus cavities just downstream from the aortic annulus. Of course, care should be taken to orient the stent 20 so as not to block the coronary openings. The stent body is preferably configured with sufficient radial strength for pushing aside the native leaflets and holding the native leaflets open in a dilated condition. The native leaflets provide a stable base for holding the stent, thereby helping to securely anchor the stent in the body. To further secure the stent to the surrounding tissue, the lower portion may be configured with anchoring members, such as, for example, hooks or barbs (not shown).

The upper portion 24 of the stent 20 has a larger diameter sized for receiving the valve member 30. A transition region 28 between the upper and lower portions of the stent body may be advantageously used to provide a seat for the bottom end of the valve member. The stent may further comprise a ridge (not shown) along an inner wall for providing a more definite seat portion within the stent.

Figure 2:
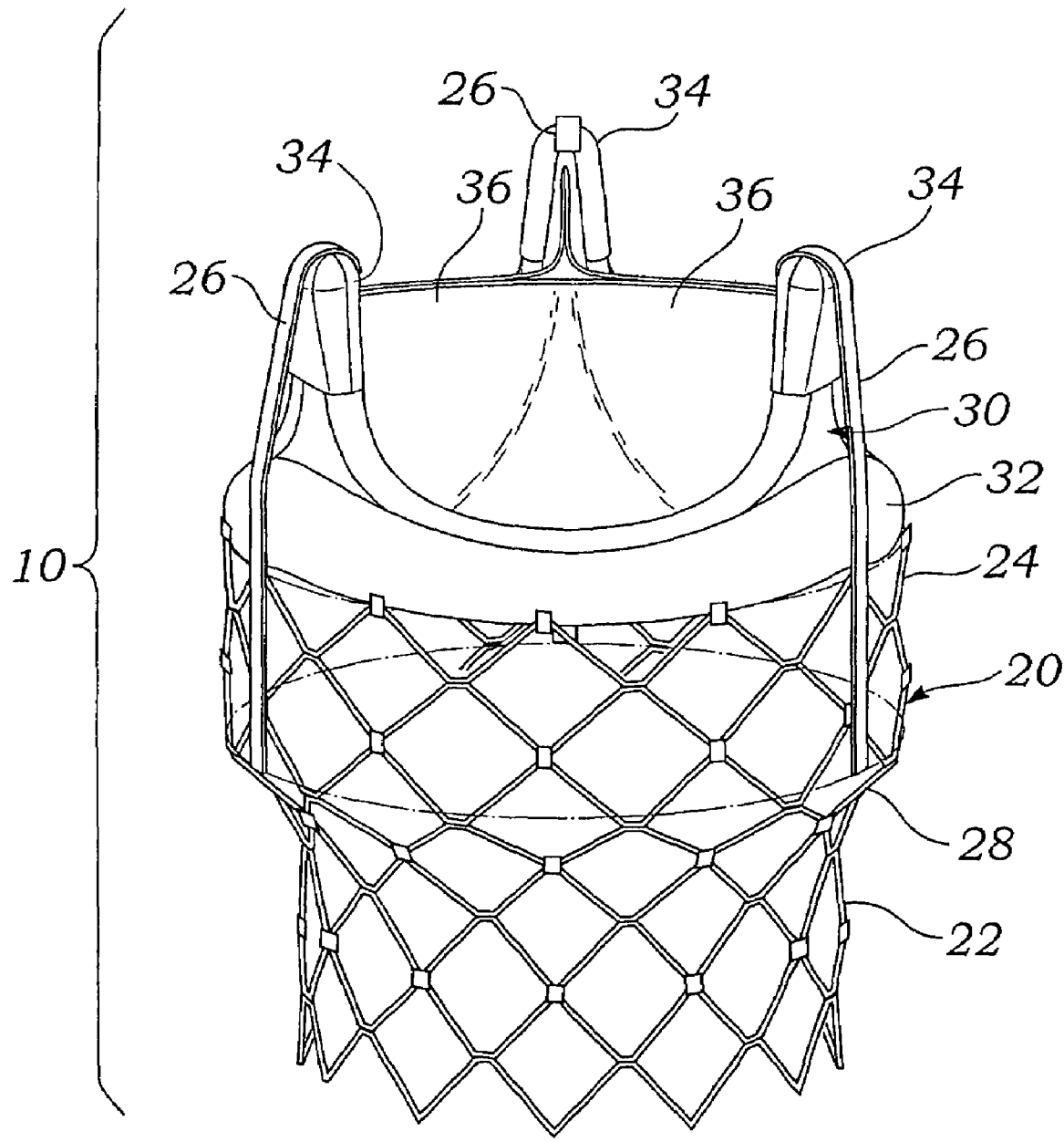
FIG. 2 illustrates the valve embodiment of FIG. 1 after the valve member has been attached to the stent portion by crimping portions of the stent over the commissural points of the valve member.

With continued reference to FIG. 1, the prosthetic valve 10 is provided with a coupling mechanism for securing the valve member 30 to the stent 20. The coupling mechanism may take a variety of different forms. However, in the illustrated embodiment, the stent body comprises three posts 26 which correspond to the three commissural points 34 on the valve member. The three posts 26 are preferably formed of a malleable material such that the posts 26 may be crimped over the commissural points on the valve member. A bending tool (not shown) may be provided for crimping the posts 26 over the commissures of the valve member, or the posts 26 may be hinged or made of the shape memory material so as to curl once implanted in the body. With reference to FIG. 2, the prosthetic valve 10 is illustrated in the assembled condition with the posts 26 crimped over the commissural points 34 of the valve member. In one variation, the three posts on the stent are formed with a recess for receiving the commissural points, such as in a snap-fit relationship.

In a preferred embodiment, the stent 20 is expandable, but the valve member 30 is a conventional, non-expandable prosthetic heart valve, such as the Carpentier-Edwards PERIMOUNT Magna® Aortic Heart Valve available from Edwards Lifesciences of Irvine, Calif. In this sense, a "conventional" prosthetic heart valve is an off-the-shelf (i.e., suitable for stand-alone sale and use) non-expandable prosthetic heart valve having a sewing ring capable of being implanted using sutures through the sewing ring in an open-heart procedure. An implant procedure therefore involves first delivering and expanding the stent 20 and the aortic annulus, and then coupling the valve member 30 thereto. Because the valve member 30 is non-expandable, the entire procedure is typically done using the conventional open-heart technique. However, because the stent 20 is delivered and implanted by simple expansion, the entire operation takes less time. This hybrid approach will also be much more comfortable to surgeons familiar with the open-heart procedures and conventional heart valves. Moreover, the relatively small change in procedure coupled with the use of proven heart valves should create a much easier regulatory path than strictly expandable, remote procedures.

A variation of the embodiment described in FIGS. 1 and 2 may incorporate an expandable stent 20 and an expandable valve member 30. Although not shown, the valve member 30 may be capable of expansion within the body, such as the Cribier-Edwards Aortic Percutaneous Heart Valve, also available from Edwards Lifesciences. Therefore, the valve 10 may be implanted without an open-heart procedure, and even without stopping heart. In such a remote procedure, the three posts 26 on the stent 20 may be made of a shape memory material having a temperature-induced shape change once implanted. Alternatively, a tool for bending the posts 26 may be delivered along with the valve 10 and utilized when the valve member 30 seats within the stent 20.

Figure 3:
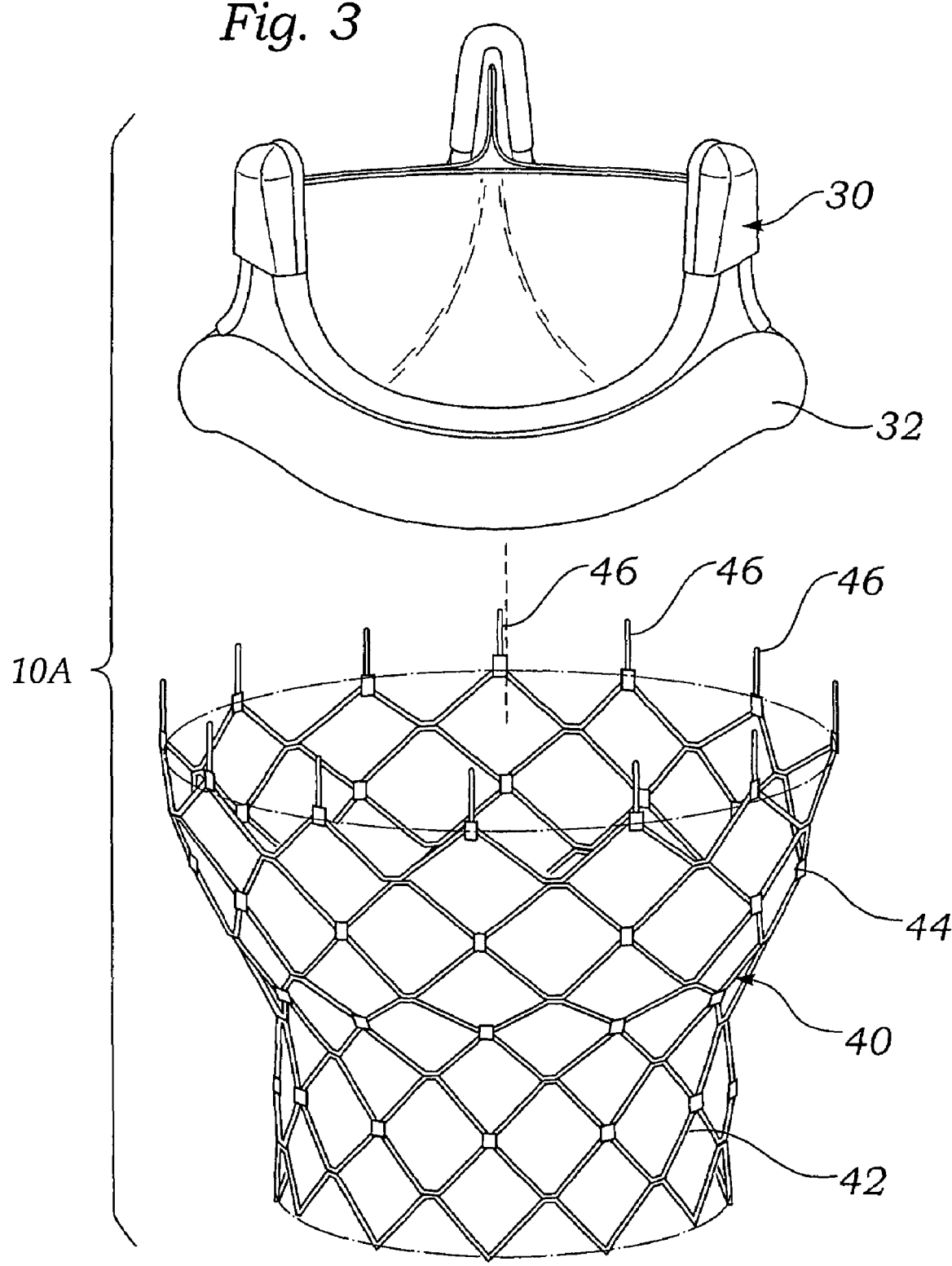
FIG. 3 is an exploded perspective view of an alternative embodiment wherein the stent is provided with a plurality of tines configured to be crimped to a ring along the base of the valve member.
Figure 4A:
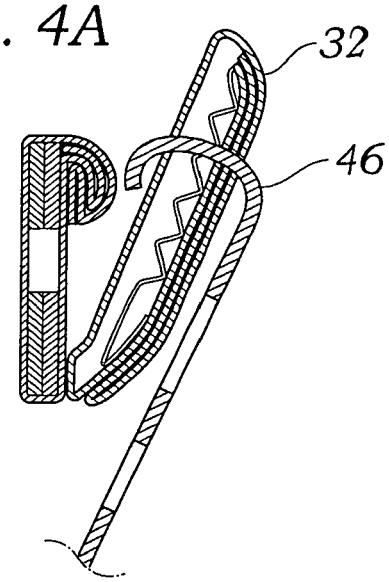
FIG. 4A is a sectional view through one side of the prosthetic heart valve of FIG. 4 taken along line 4A-4A and showing one configuration of tines connecting through a sewing ring portion of the valve member.
Figure 4:
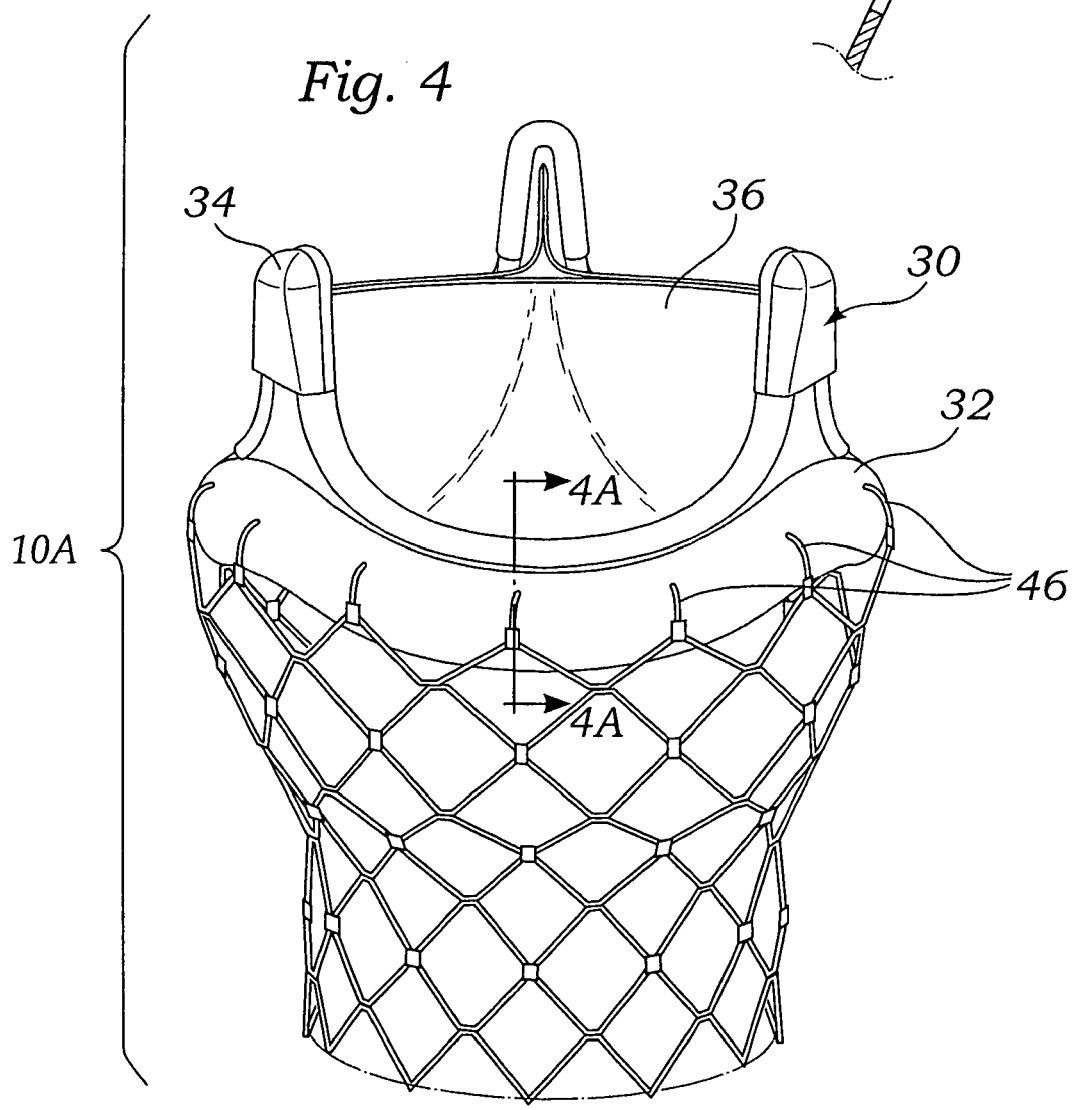
FIG. 4 illustrates the valve embodiment of FIG. 3 after the valve member has been attached to the stent portion by crimping the tines on to the valve member.

With reference now to FIG. 3, an alternative prosthetic valve 10A comprises a stent 40 provided with a bottom portion 42 and an upper flared portion 44. A plurality of prongs or tines 46 is disposed along a top end of the flared portion 44. The tines 46 are preferably bendable members configured to engage the ring portion 32 along the base of the valve member 30. In one preferred embodiment, the tines 46 are crimped over the ring as shown in FIG. 4. If desired, the tines 46 may have pointed tips for passing through a fabric or other similar material along the ring portion of the valve member, such as seen in FIG. 4A.

Once again, the stent 40 is desirably an expandable member that can be easily delivered and implanted at the body channel. The valve member 30 may be conventional, or may also be expandable. The illustrated embodiment shows a conventional valve 30 having the sewing ring portion 32 surrounding an inflow end. Sewing rings are typically made of suture-permeable material covered with cloth. The tines 46 may be sharp enough to pierce the material of the sewing ring portion 32 (FIG. 4A). In this regard, a conventional valve member 30 may be utilized without modification. In the alternative, the sewing ring portion 30 may be replaced with a more rigid peripheral band or ring, and the tines 46 are simply bent inward so as to fold over the ring and capture the valve member 31 on the top of the stent 40. Desirably, a seat or rim of some sort is provided within the interior of the stent 40 so that the valve member 30 can easily be positioned therein. The tines 46 may be mechanically bent using a deployment tool (not shown), or they may be hinged or made of a shape memory material so as to curl inward upon reaching a certain temperature.

Figure 5A:
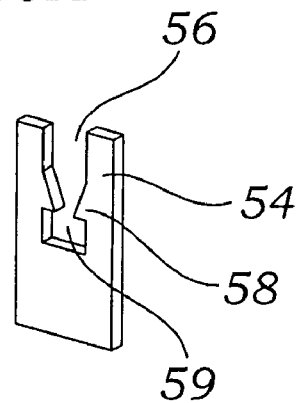
FIG. 5A is an enlarged view of one of the slotted posts provided on the stent of FIG. 5.
Figure 5:
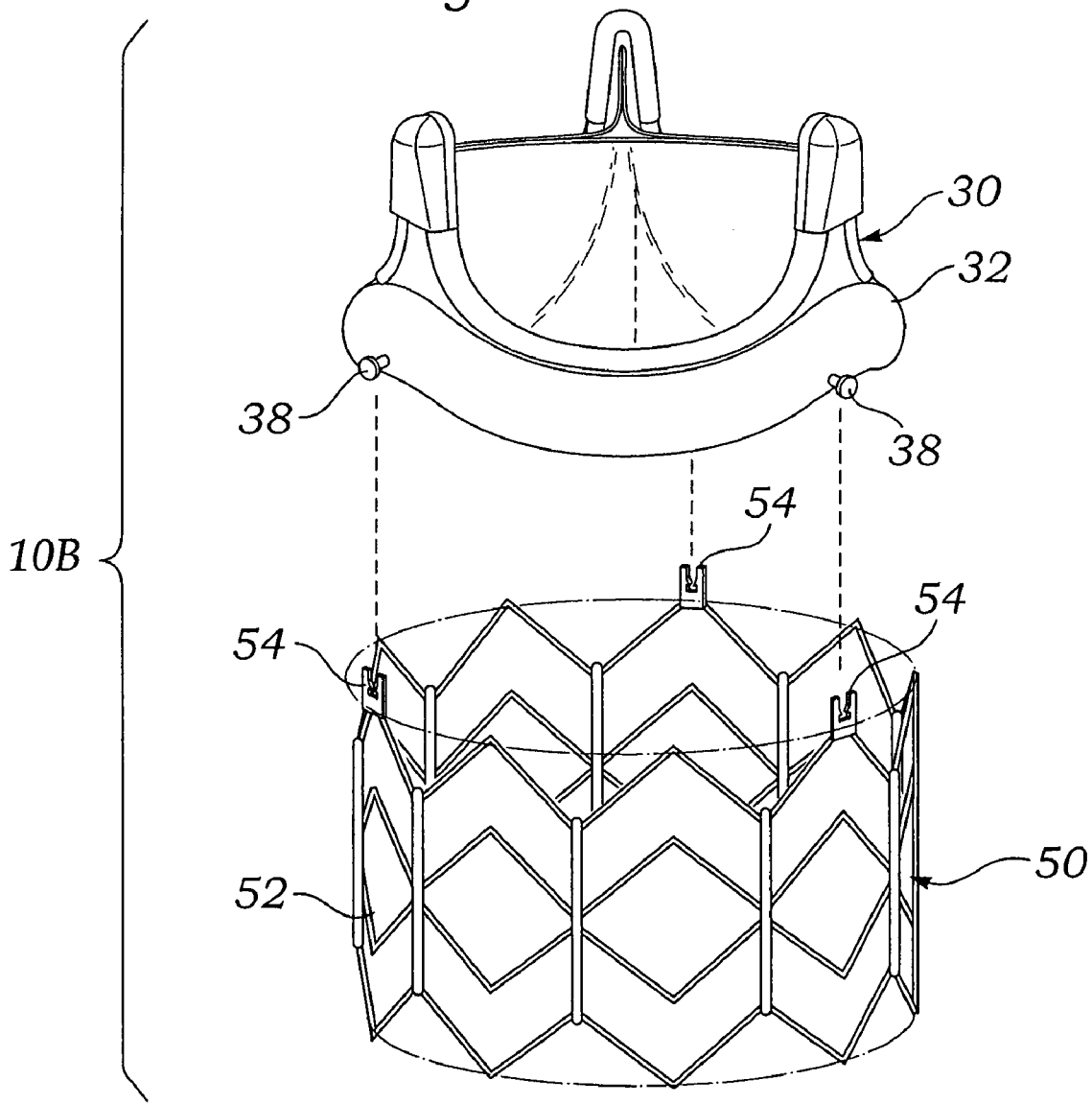
FIG. 5 is an exploded perspective view of an alternative embodiment wherein slotted posts are provided on the stent for coupling to protruding members on the valve member.

With reference now to FIG. 5, another alternative prosthetic valve 10B comprises an anchoring member or stent 50 provided with a cylindrical portion 52 and three posts 54 extending upward from the cylindrical portion. Each post 54 may be slotted, as illustrated in the enlarged view of FIG. 5B, or formed with an orifice. Radially protruding members 38 are provided along the ring portion 32 of the valve member 30 for mating with the posts on the stent. The exemplary slot has a thin neck portion 58 wherein engagement members, such as angled teeth, are provided. The teeth are angled such that the slot widens as the protruding member 38 is pushed downward into the slot. After passing through the teeth into the capture portion 59, the protruding member 38 is securely captured. Because the teeth are angled in only one direction, an upward force will not cause the slot to widen, thereby capturing the protruding member.

Figure 6A:
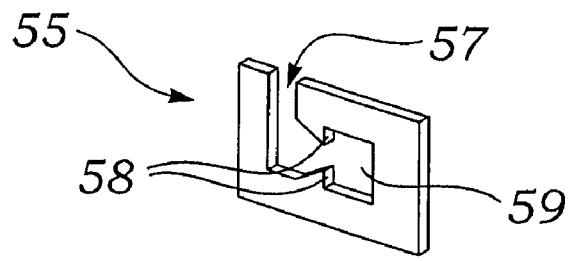
FIGS. 6 and 6A illustrate another alternative embodiment similar to FIGS. 5 and 5A wherein the posts are configured with L-shaped slots for locking the valve member to the stent.
Figure 6:
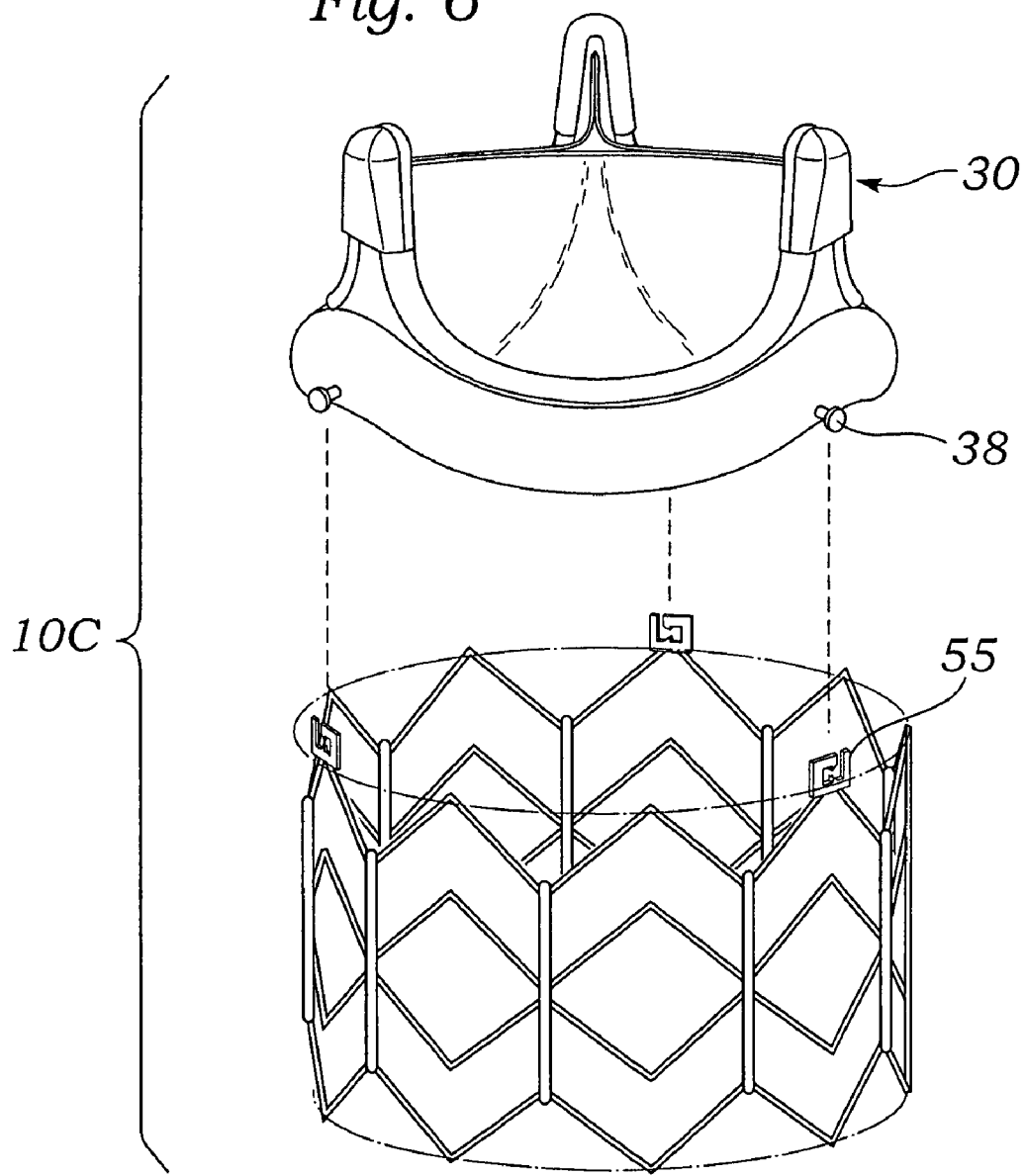

With reference now to FIG. 6, yet another alternative embodiment of a component prosthetic valve 10C is illustrated. The embodiment of FIG. 6 is similar to the embodiment illustrated and described above with respect to FIG. 5. However, in this variation, the posts or connecting members 55 are provided with L-shaped slots 57 for receiving the protruding member disposed along the valve member. With reference to FIG. 6A, an enlarged view of one preferred connecting member 55 is shown. The slot 57 of the connecting member 55 is shaped such that the protruding member 38 moves longitudinally into the slot and then rotationally to enter the capture portion. One or more teeth 58 may be provided for holding the protruding member in the capture portion. Alternatively, the protruding member 38 may be held in the slot 57 using friction or a mechanical locking member. In another alternative, a key lock system or "bayonet" attachment mechanism may be provided for coupling the valve member to the stent.

Figure 7:
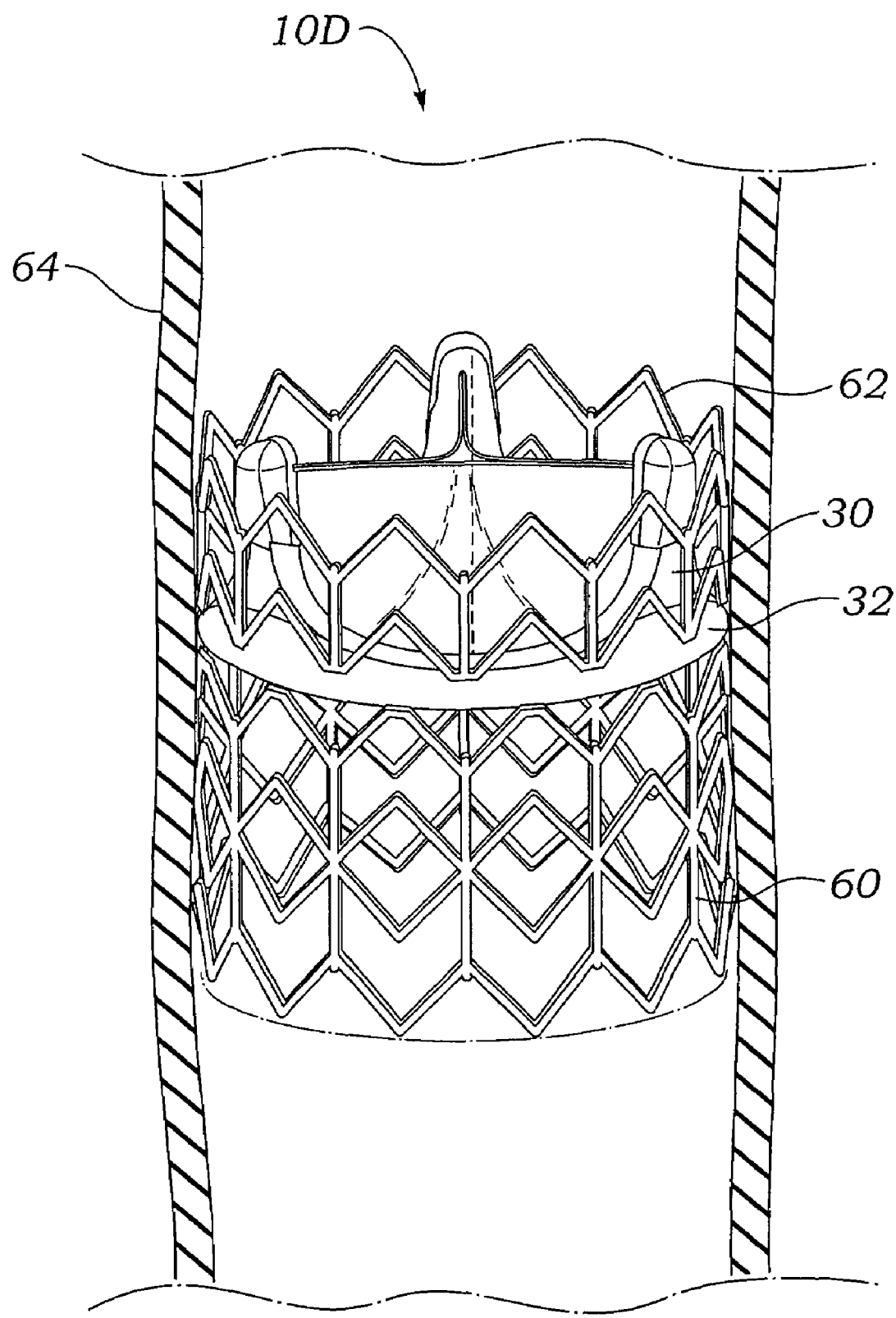
FIG. 7 is a sectional view through a body channel that illustrates an alternative embodiment of prosthetic heart valves wherein first and second stents are provided for anchoring a valve member within the body channel.

With reference now to FIG. 7, another alternative prosthetic valve 10D is illustrated wherein the valve member 30 is captured and held between first and second stents 60, 62. In use, the first stent 60 is expanded within a body channel such that the outer surface of the stent is in contact with the vessel wall 64. The valve member 30 is then advanced through the body channel and into contact with the first stent. A ring 32 is preferably provided along the base portion of the valve member for contacting the outflow end of the first stent. The second stent is then advanced through the body channel and is deployed such that an inflow end of the second stent contacts a top surface of the ring 32 of the valve member for anchoring the valve member between the first and second stents.

The embodiment of FIG. 7 employs a slightly different means for connecting the valve member 30 the anchoring member. Primarily, stents 60, 62 capture the ring 32 of the valve member 30 therebetween simply by providing upper and lower barriers to movement. The valve member 30 is desirably a non-expandable type, therefore the ring 32 is not overly susceptible to compression. By providing sufficient of the thickness of the stents 60, 62, the valve member 30 remains sandwiched therebetween. In this regard, the outflow end of the first stent 60 and the inflow end of the upper stent 62 are preferably flat or blunt so as not to dig into the ring 32. Because of the anchoring function of the stents 60, 62, there is no need to suture the valve member 30, and thus the ring 32 may be made relatively firm or rigid. Alternatively, the facing edges of the stents 60, 62 may be provided with barbs or other such piercing devices, and the ring 32 provided as a conventional suture-permeable sewing ring.

As noted above, the anchoring members or stents described herein could include barbs or other anchors to further secure the stent to the tissue. Further, the barbs could be deployable (e.g., configured to extend or be pushed radially outward) by the expansion of a balloon. Likewise, the stent can be covered to promote in-growth and/or to reduce paravalvular leakage. The cover would be similar to those on other valves, e.g., a Dacron tube or the like.

Alternatively, the valve member may be constructed with a tubular frame or cage for engaging one or both stents 60, 62. In various preferred embodiments, the stents may be self-expanding or balloon-expandable. In one advantageous feature, the valve member 30 of this embodiment is not required to be mounted within a cylindrical frame or stent. Accordingly, the flow through area of the valve member may be maximized to improve valve function. In another variation, the first and second stents may be integrated as a single unit forming a chamber therebetween. In this variation, the valve member may be expanded within the chamber for securely deploying the valve member in the body channel.

Figure 8:
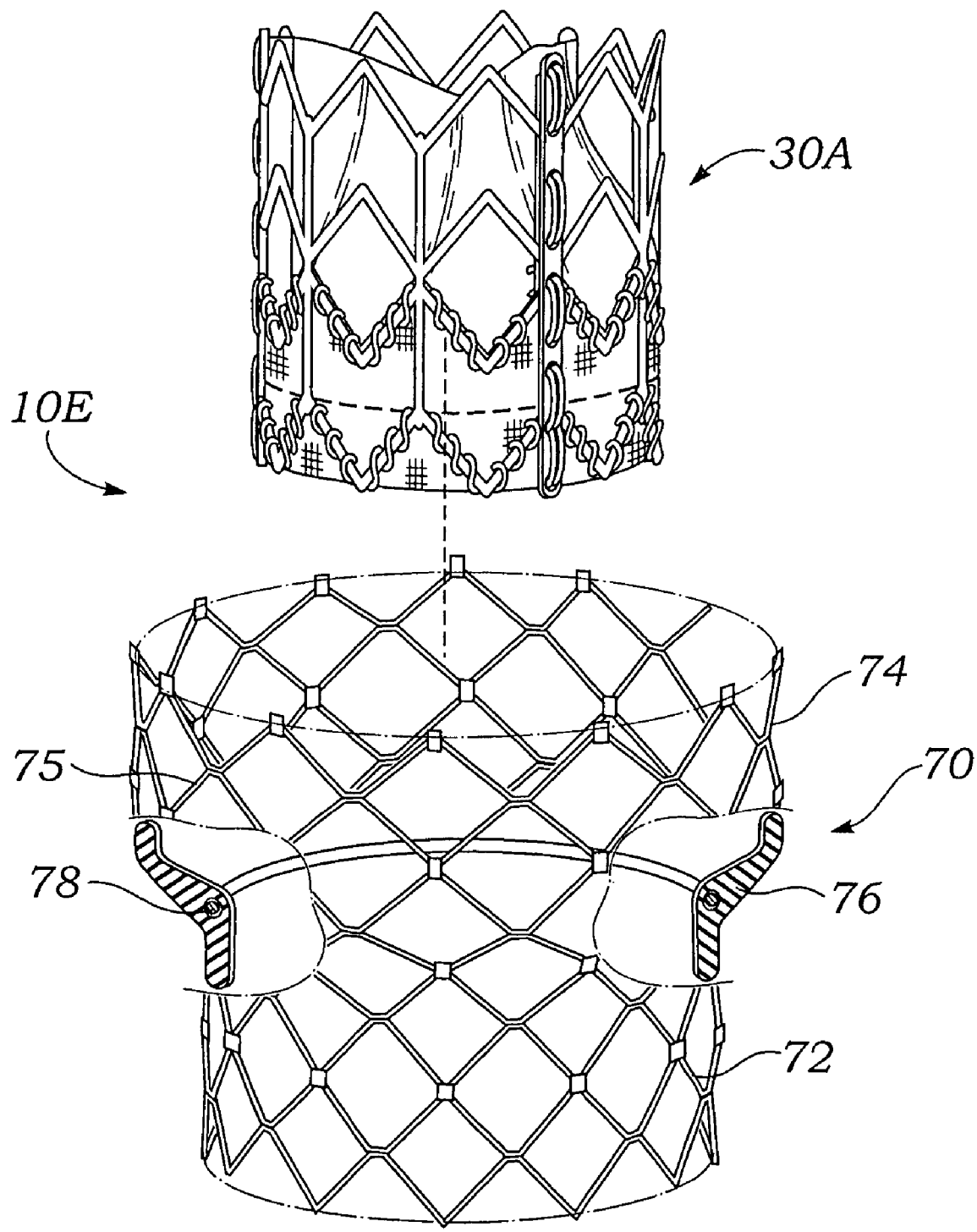
FIG. 8 is an exploded perspective view of an alternative embodiment wherein the stent has a small diameter and a large diameter and wherein an expandable valve member is deployed within the large diameter.

With reference now to FIG. 8, another alternative embodiment of a two-stage prosthetic valve 10E is illustrated wherein the anchoring member or stent 70 is provided with a varying diameter. More particularly, a lower portion 72 of the stent has a small diameter sized for implantation at a native valve annulus. In one preferred configuration, the small diameter is about 23 mm. The stent also has an upper portion 74 with a larger diameter for receiving an expandable valve member 30A. In one preferred configuration, the larger diameter is about 29 mm. In this embodiment, the valve member 30A is provided as a tubular body that is radially expandable. The valve leaflets are disposed along the interior of the valve member.

The stent 70 preferably includes a circular ridge 76 formed along the transition region between the large and small diameters. The ridge provides a seat for the base of the valve member 30A. In one preferred embodiment, the ridge 76 incorporates a support wire 78 that extends at least partially through the ridge for strength and may be used to provide a radiopaque marker. The remaining portion of the ridge may be formed of Dacron or any other suitable material. The stent 70 may be comprised of a screen or mesh. A cover 75, such as a polymer sheet, may be provided along at least a portion of the stent to help prevent leakage and enhance sealing. In addition, a sponge or cloth may be provided along the exterior portion of the stent for further enhancing sealing.

The stent 70 of FIG. 8 may be self-expanding or balloon-expandable. When provided as a balloon-expandable stent, a expandable tapered (i.e., two diameter) balloon may be provided for deploying the stent. When configured for use with a stent having diameters of 23 mm and 29 mm, the balloon may have diameters of 22 mm and 28 mm, respectively.

Figure 9:
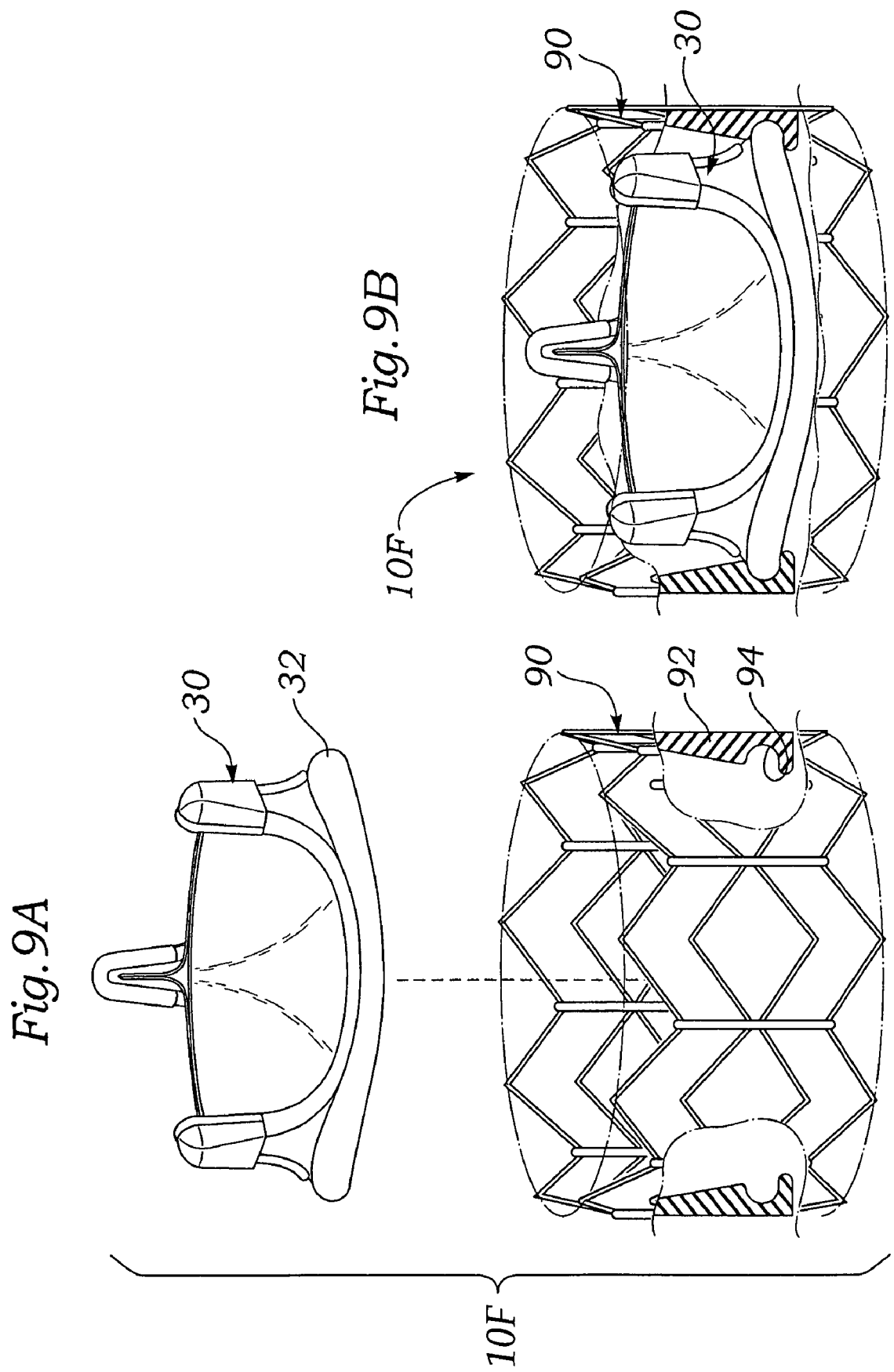
FIG. 9A is an exploded perspective view of another alternative embodiment of a two part prosthetic valve wherein a ring portion along the base of the valve member snaps into a groove formed in the stent.
FIG. 9B illustrates the embodiment of FIG. 9A with the valve member connected to the stent.

With reference now to FIGS. 9A and 9B, another alternative embodiment of a component prosthetic valve 10F is provided wherein a valve member 30 is configured for connection with an anchoring member or stent 90. In this embodiment, the stent 90 is provided with a groove 94 formed in an inwardly-directed circumferential member 92. The groove extends at least partially around the inner portion of the stent and is sized to receive the ring portion 32 of the valve member 30. In one preferred embodiment, the ring is configured to snap fit into the groove, as seen in FIG. 9B. In another variation, the ring is made of a shape memory material configured to expand after deployment in the body. In this variation, the ring is configured to radially expand for securely anchoring itself within the groove.

Figure 10:
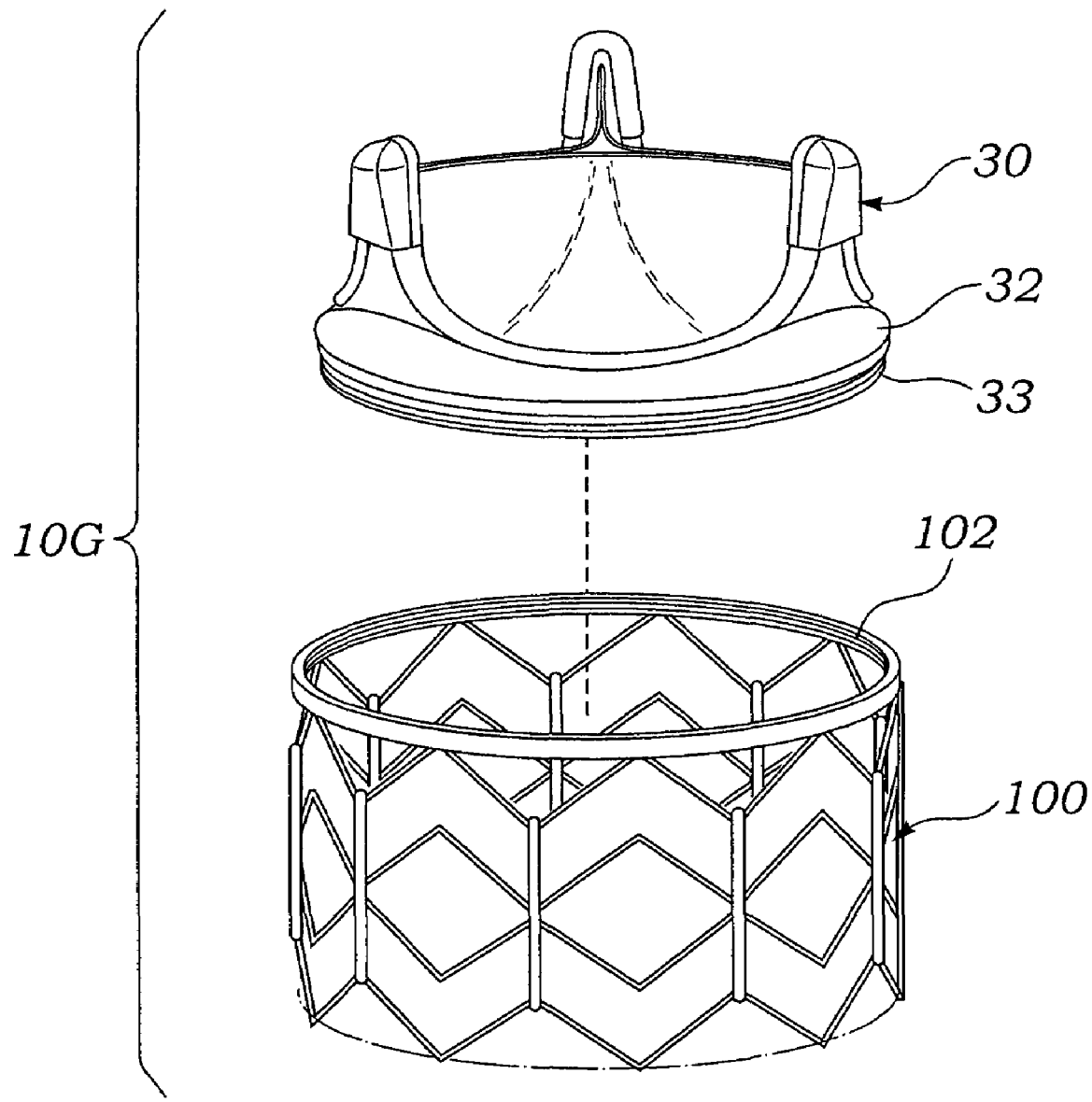
FIG. 10 is an exploded perspective view of another alternative embodiment wherein the valve member and the stent are provided with corresponding threaded portions for threadably engaging the valve member to the stent.

With reference now to FIG. 10, yet another alternative embodiment of a component prosthetic valve 10G is illustrated wherein the valve member 30 is configured for threadable engagement with an anchoring member or stent 100. In this embodiment, the stent is provided on one end with a threaded region 102 along an inner wall configured for receiving a threaded flange portion 33 on the valve member 30. The threaded flange portion is preferably provided along the ring 32 at the base of the valve member. During use, the stent is first deployed in the body channel. The stent may be deployed in a manner wherein the diameter of the threaded region remains substantially constant so as to not affect the threads. In one embodiment, the stent is substantially non-expandable and is delivered into the lumen in its fully expanded condition. This can be achieved by first stretching or dilating the delivery site for receiving the stent. In another embodiment, only the lower portion of the stent is expanded for engaging the tissue. In either embodiment, the valve member is threadably attached to the threaded flange on the stent after the stent has been firmly anchored in the body channel. This attachment means is configured such that the valve member advantageously connects to the stent through rotational movement. Accordingly, longitudinal forces applied to the valve member after implantation will have little or no effect on the integrity of the connection between the stent and valve.

With reference now to FIG. 11, an alternative prosthetic heart valve 10H comprises a valve member 30, an anchoring member or stent 110, and a locking ring 112. As before, the stent 110 desirably expands first at the implantation site, after which a conventional valve member 30 couples to the stent through the use of the locking ring 112. However, the valve member 30 may also be expandable, and the stent 110 can take a variety of forms. In a preferred embodiment, the stent 110 comprises a latticework of balloon-expandable members adapted to be delivered to the implantation site in a collapsed or compressed state, and then expanded from within using a balloon. Of course, a self-expanding stent 110 could also be used, and additional anchoring means of such as exterior barbs may be provided to help prevent the stent from migrating after implantation.

A series of tabs or flanges 114 project slightly inwardly from an outflow end of the stent 110. The flanges 114 are configured to mate with exterior threading 116 on a downwardly-projecting shoulder of the locking ring 112. The number and configuration of the flanges 114 is selected to avoid interfering with radial expansion of the stent 110, and also to mate with the threads 116 of the locking ring 112. Desirably, a series of space-apart flanges 114, for example eight, evenly spaced around the outflow rim of the stent 110 project inward therefrom a distance of between 1-3 mm.

An inner bore 118 of the locking ring 112 possesses a diameter large enough to pass over the entire valve member 30 except for the base ring 32, which could be a sewing ring of a conventional heart valve. When coupled together, the locking ring 112 surrounds the valve member 30 and desirably includes an inner ledge that rests on the base ring 32 thereof. The inner diameter of the shoulder having the exterior threading 116 is sized larger than the base ring 32 and extends downwardly into engagement with the flanges 114. By screwing down the locking ring 112, the components can be easily and rapidly assembled. After implantation, removal and replacement of the valve member 30 merely requires releasing the locking ring 112 from any tissue ingrowth, unscrewing and removing it, and releasing the valve member 30 from the stent 110 by cutting away any tissue ingrowth therebetween.

FIGS. 12A and 12B illustrate another prosthetic heart valve 10I of the present invention having an expandable anchoring member or stent 120 coupled to a valve member 30. Much like the valve 10A of FIGS. 3 and 4, the outflow end of the stent 120 exhibits a series of spaced-apart tabs 122 that curl around the base ring 32 of the valve member 30. In this embodiment, the stent 120 is a straight tube, and there are fewer tabs 122 (e.g., eight) than there are tines 46 in the valve 10A. The tabs 122 may be bent using an auxiliary tool (not shown), or may possess a property permitting autonomous bending, such as temperature-induced movement.

Figure 12C:
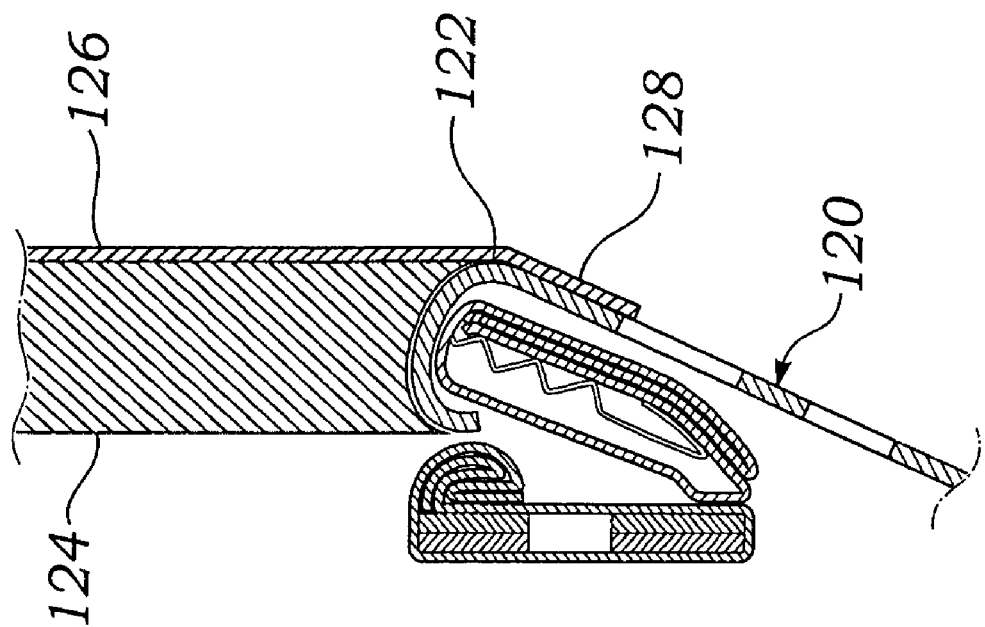
FIGS. 12C and 12D are sectional views through one side of the prosthetic heart valve of FIG. 12B schematically illustrating an exemplary tool that may be used to bend the tabs on the outflow end of the stent around a sewing ring of the valve member.
Figure 12D:
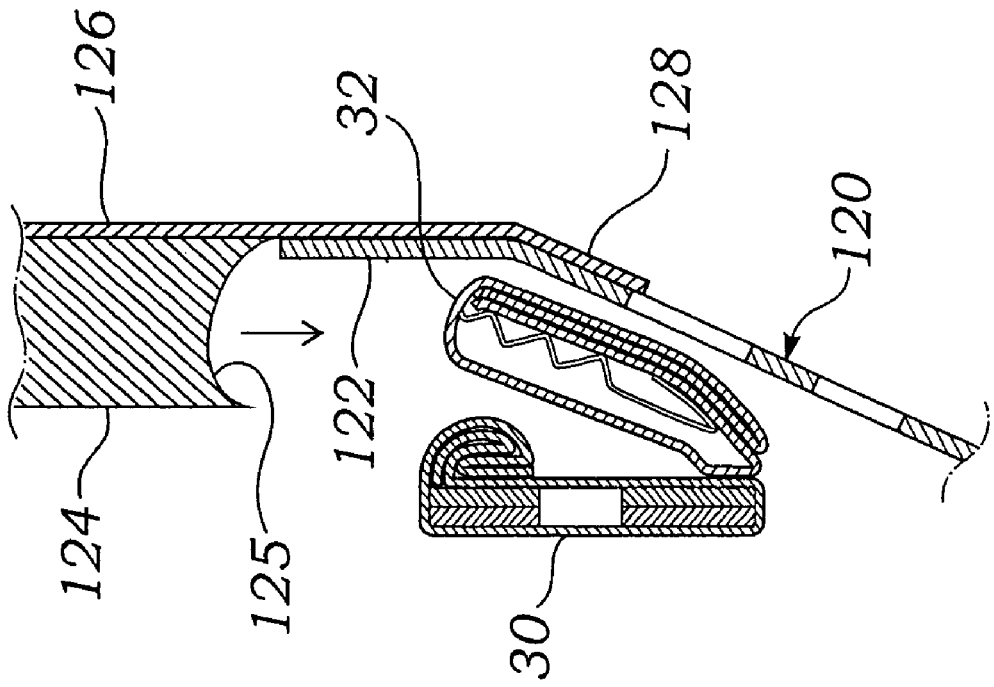

FIGS. 12C and 12D are sectional views through one side of the prosthetic heart valve 10I of FIG. 12B schematically illustrating an exemplary tool that may be used to bend the tabs 122 on the outflow end of the stent 120 around the base ring 32 of the valve member 30. It should be noted that the section is taken radially through one side of the system, and the tool will typically be annular or at least peripherally arranged to bend each one of the tabs 122. The tool comprises a forming member 124 having a forming surface 125. The forming member 124 slides within and relative to an outer anvil 126 having an inwardly angled portion 128 that directly surrounds and engages each of the tabs 122. The forming surface 125 is curved such that axial displacement of the forming member 124 in the direction shown in FIG. 12C curls each of the tabs 122 inward to the shape of FIG. 12D. In this embodiment, the tabs 122 wrap over the top of and restrain the base ring 32. In other embodiments, the tool may be used to bend prongs so that they pierce the base ring 32. It should be noted that the outer anvil 126 is primarily used for centering purposes to guide the forming member 124 toward the tabs 122.

Figure 13A:
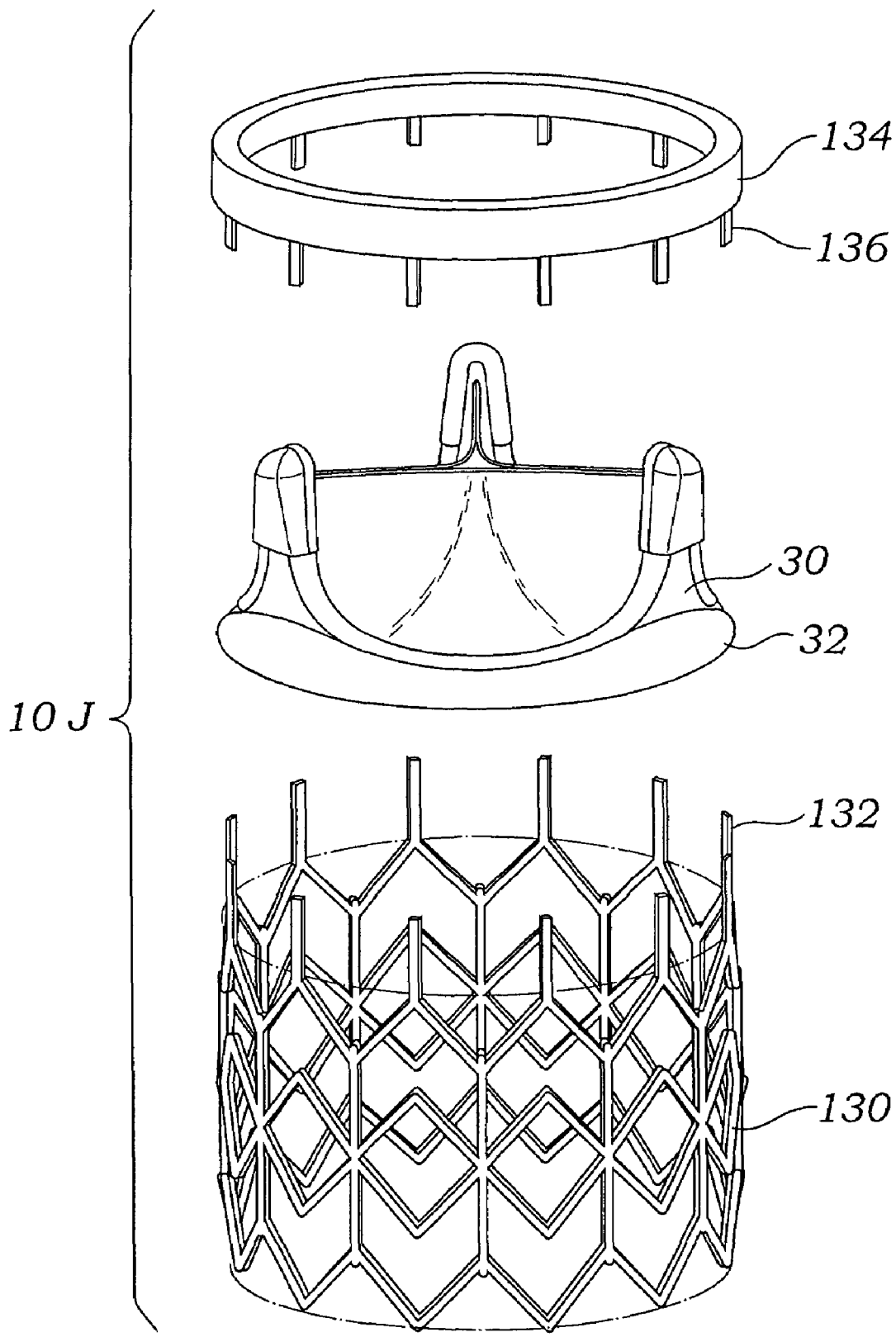
FIGS. 13A and 13B are exploded and assembled perspective views of an alternative prosthetic heart valve of the present invention wherein a valve member and stent with tabs are coupled together in conjunction with a locking ring.
Figure 13B:
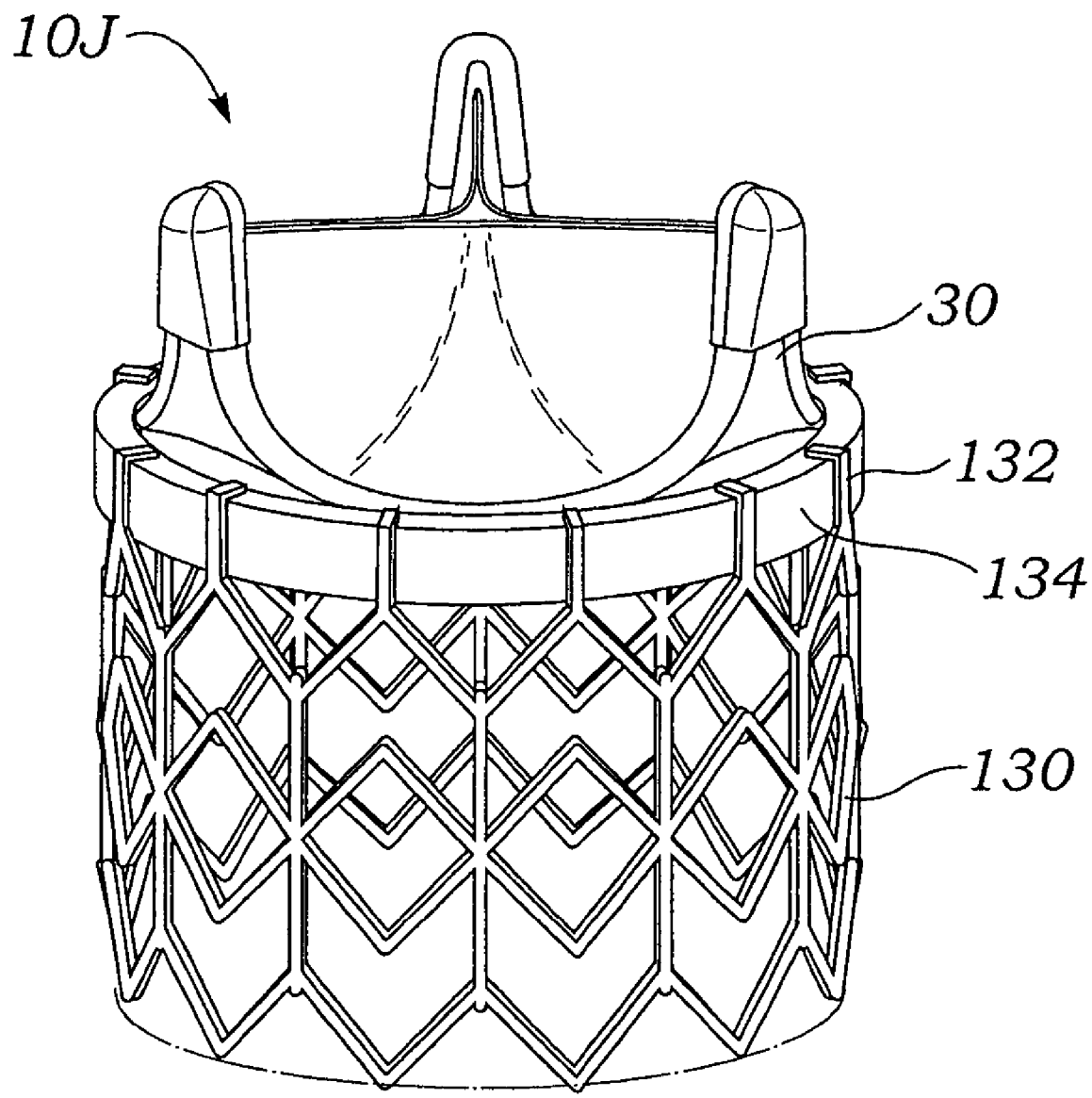

FIGS. 13A and 13B illustrate another embodiment of a prosthetic valve 10J having multiple components joined together. An anchoring member or stent 130 includes a plurality of tangs or flanges 132 on an outflow end. A valve member 30 seats adjacent the outflow end of the stent 130, and a fixation ring 134 extends therearound. Additionally, a plurality of tabs 136 project downward from the fixation ring 34. Although not shown, the tabs 136 enable the fixation ring 34 to be coupled to the base ring 32 of the valve member 30 by mechanically bending the tabs, or configuring the tabs to curl upon reaching a certain temperature. As seen in FIG. 13B, the flanges 132 extend around the outside of the fixation ring 134 and bend around the upper or outflow end thereof. Again, this can be accomplished using an auxiliary tool or through temperature-induced movement. Alternatively, the flanges 132 may be formed of a resilient polymer or metal having the shape seen in FIG. 13B such that they can be flexed outward around the fixation ring 134 and then snapped back into place to secure the ring around the valve member 30. Although not shown, the interior of the fixation ring 134 is desirably contoured to mate with the base ring 32 of the valve member 30. The fixation ring 134 can be made of any number of materials, including rigid, flexible, metallic, polymer, bioabsorbable, etc. One preferred configuration is a Teflon ring coated with anti-thrombogenic or anti-microbial compositions.

Figure 14A:
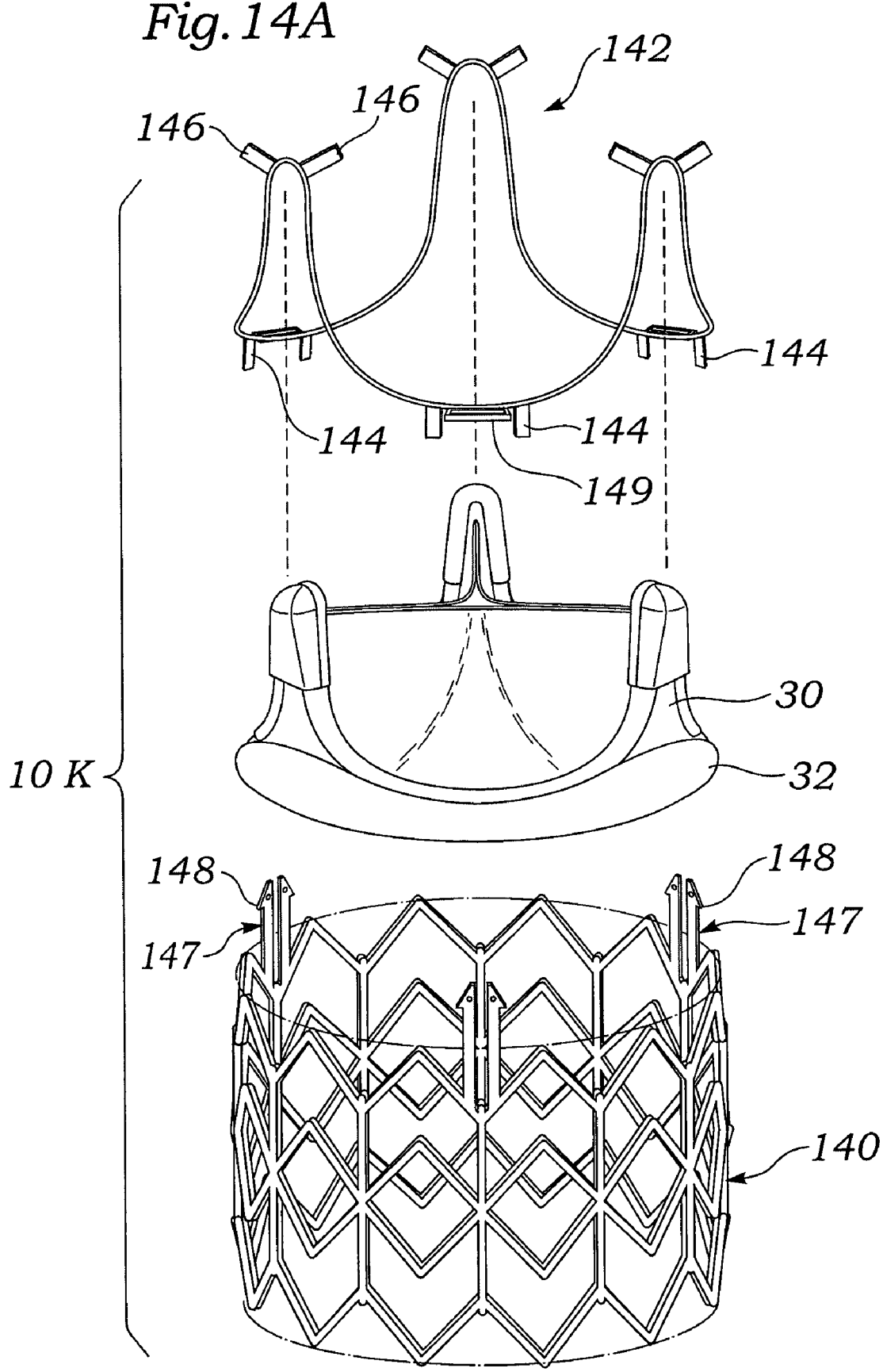
FIGS. 14A and 14B are exploded and assembled perspective views of a still further prosthetic heart valve wherein a valve member and tubular, expandable stent are coupled together using a wireform-shaped adapter having tabs.

FIG. 14A illustrates a still further prosthetic heart valve 10K having an expandable anchoring member or stent 140, a valve member 30, and a wireform-shaped adapter 142. The stent 140 and valve member 30 have been previously described. The adapter 142 has a shape similar to a so-called "wireform" used in the internal construction of many prior art bioprosthetic tissue valves. Indeed, the valve member 30 is desirably a Carpentier-Edwards PERIMOUNT Magna® Aortic Heart Valve made by Edwards Lifesciences, and including therewithin an Elgiloy wireform. The adapter 142 may be formed of biocompatible polymers or metals, preferably an alloy such as Nitinol.

Figure 14B:
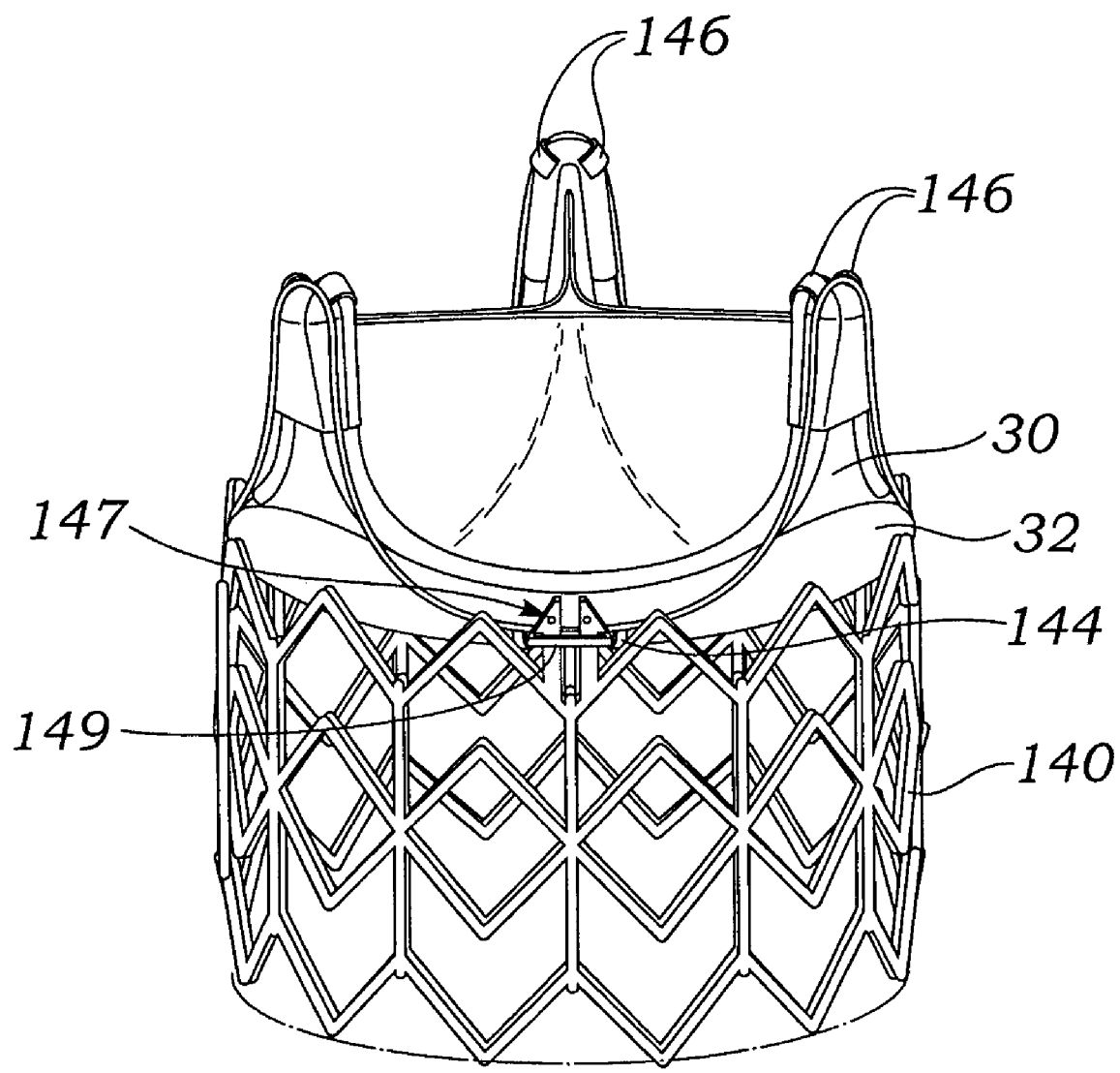

The adapter 142 carries a plurality of securing tabs 144, 146. In the illustrated embodiment, three lower securing tabs 144 are located at the apex of the three cusps of the wireform-shape, and two upper securing tabs 146 are located at each of the upstanding commissures of the wireform-shape, for a total of six at the commissures. FIG. 14B is a detailed illustration of the assembly of the stent 140, valve member 30, and adapter 142. The base ring 32 of the valve member 30 seats on or just within the outflow end of the stent 140, and the adapter 142 fits over the valve member and couples to it, as well as to the stent. In this regard, the cusps of the adapter 142 seat on or slightly outside the base ring 32 with the commissures surrounding and conforming to the commissures of the valve member 30. The cusp securing tabs 144 bend up over the base ring 32 and down into engagement with the stent 140. The two securing tabs 146 at each commissure of the adapter 142 bend or wrap around the corresponding valve member commissure.

Again, a supplemental tool may be used to accomplish the bending of the securing members 144, 146, or they may exhibit temperature-changing properties. In the illustrated embodiment, the securing tabs 144, 146 are malleable, though other configurations are within the scope of the invention. For example, the lower securing tabs 144 may be barbs or tangs which pierce the base ring 32 and hook around the stent 140, while the upper securing tabs 146 may be resilient straps that wrap around each one of the commissures of the valve member 30.

To further secure the valve member 30 to the stent 140, the stent includes a plurality of upstanding barbs 147 comprising spaced apart posts having teeth 140. The adapter 142 possesses a plurality of outwardly projecting brackets 149 defining slots therethrough. As seen in FIG. 14B, the barbs 147 pass through the base ring 32 and through the slots of the brackets 149 in the adapter 142. The teeth 148 prevent removal of the barbs 147 from the slots. In this way, the stent 140 and adapter 142 are securely connected together, sandwiching the valve member 30 therebetween.

Another possibility is that the securing tabs 144, 146 are not initially carried by the adapter 142, but instead are added after the assembly of the three components. For instance, staples or even sutures may be used after the valve member 30 seats on the stent 140, and the adapter 142 is lowered around the valve member. Even if sutures are used, the time required relative to a conventional sewing operation is greatly reduced. Moreover, the structural support and anchoring properties of the wireform-shaped adapter 142 greatly enhances the overall integrity of the assembly. In this regard, securing tabs such as those shown may be placed more continuously around the adapter 142 so as to provide more uniform contact with the valve member 30. One possible configuration is a series of small hooks or brackets extending along the undulating adapter 142 that loop over the corresponding undulating shape on the valve member 30. The valve member 30 is therefore restrained from upward movement relative to the adapter simply by lowering the adapter 142 over the valve member. In such an arrangement, only the lower securing members need be actively attached, such as by causing their shape to change and bend into engagement with the stent 140, as seen in FIG. 14B.

A further prosthetic valve embodiment 10L seen in FIG. 15A includes an expandable anchoring member or stent 150 and a valve member 30. A plurality of fixation straps 152 is disposed along the outflow end of the stent 150. Four such straps 152 are shown; however, in other variations, more or less may be utilized. For example, three straps extending farther around the periphery of the outflow end of the stent 150 may be substituted. Conversely, four or more straps that overlap one another may be used.

FIG. 15B illustrates the valve member 30 seated on top of the stent 150 with one of the straps 152 securing the two components together. Straps 152 may be attached at both of their ends to the stent 150, and may comprise a resilient biocompatible material that stretches over the base ring 32 of the valve member 30. Alternatively, the straps may be bent or folded over the base ring. In one variation, one end of each strap 152 may be initially free, and after the strap is looped over the base ring 32 is then attached to the stent 150, somewhat like a belt configuration. The straps 152 may be formed of a variety of materials, typically cloth-covered so as to permit tissue ingrowth over a cloth-covered base ring 32 for enhanced long-term anchorage. One possible variation is to incorporate small barbs or Velcro-style hooks in each of the straps 152 so as to gain better purchase on the base ring 32.

Figure 16A:
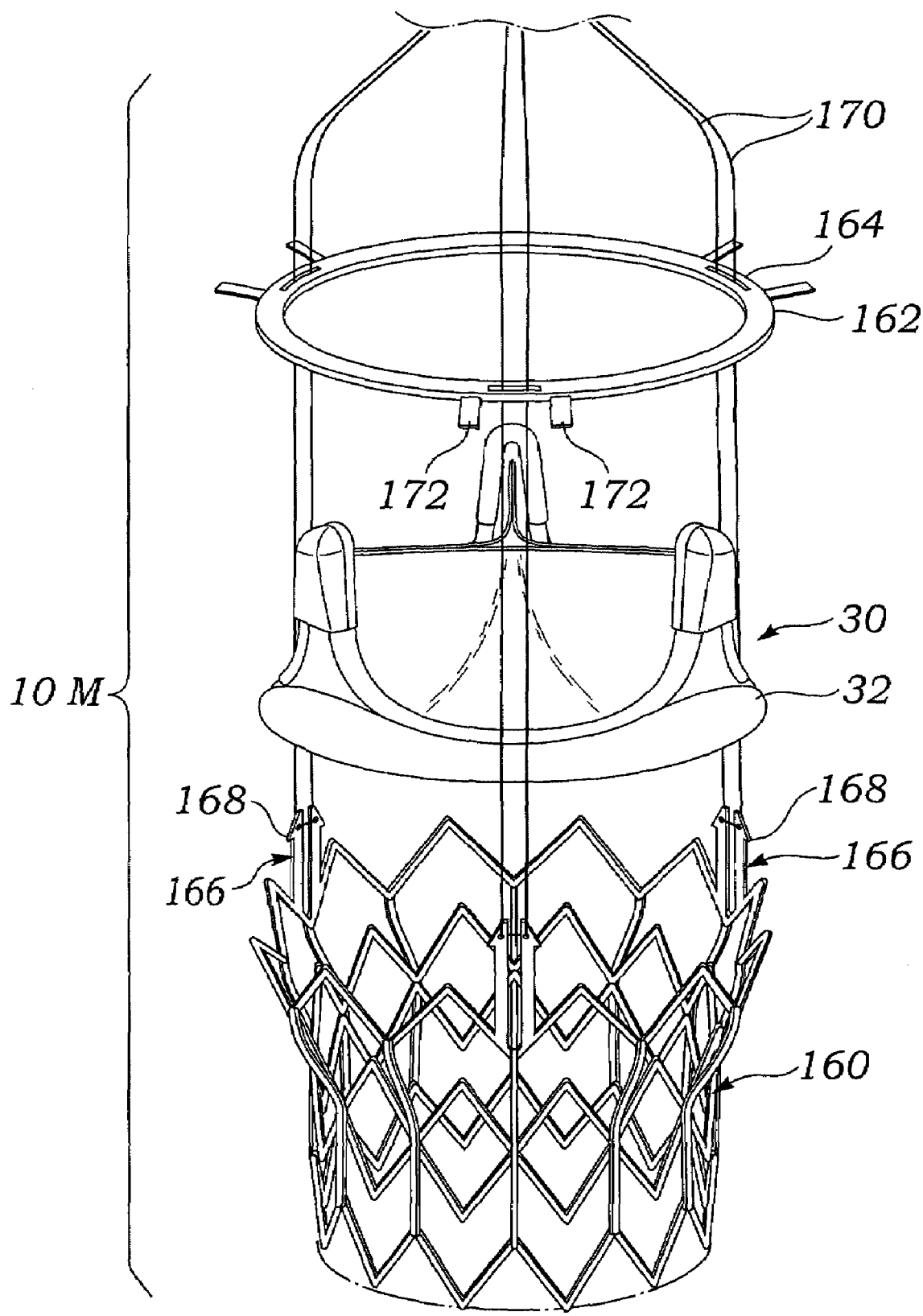

FIGS. 16A and 16B illustrate a still further embodiment, wherein the prosthetic heart valve 10M comprises a valve member 30, expandable anchoring member or stent 160, and coupling ring 162. The coupling ring 162 defines a series of circumferentially-spaced apertures or slots 164 that receive upstanding hooks or latches 166 on the stent 160. As seen in FIG. 16B, the coupling ring 162 surrounds the commissures of the valve member 30 and seats on the base ring 32, and the latches 166 extend through the slots 164 and are secured therein by outwardly directed teeth 168. In the illustrated embodiment, the latches 166 each comprise a pair of parallel, spaced apart upstanding members, each with an outwardly directed tooth 168, which may be cammed inward toward one another as they pass through the slots 164. As the teeth 168 clear the slot 164, the parallel members resiliently spring outward thus latching the stent 160 to the coupling ring 162. The coupling ring 162 may further include a plurality of outwardly projecting tabs 172 that are bent or curl around the base ring 32.

To aid in guiding the latches 166 through the slots 164, one or more guide members may be used to direct the coupling ring toward the stent such that the slots are aligned with the latch members. For example, in the illustrated embodiment, a plurality of guide filaments 170 are attached to each one of the upstanding latch members and passed through the corresponding slots. FIG. 16A illustrates the pre-assembled valve 10M with the guide filaments 170 extending up through each of the slots 164. The implantation procedure comprises first delivering and expanding the stent 160, and then advancing the valve member 30 to the position shown in FIG. 16B. The coupling ring 162 is then parachuted down the array of guide filaments 170, ultimately facilitating passage of the latches 166 through the slots 164. The final assembly is seen in FIG. 16B, in a preferred embodiment, each two guide filaments 170 comprises a strand of a single looped passing through small holes in each of the latch members. Removal of the guide filaments 170 is thus a simple matter of just pulling one of the strands, or severing the loop in between the latch members. Note that guide filaments could be used on any of the embodiments described herein to facilitate coupling of the separate components of the prosthetic heart valves. For example, in another variation, a wireform similar to the embodiment illustrated in FIG. 14A may also be used with a guiding filament.

The exemplary embodiment shows the latches 166 extending around the outside of the base ring 32 of the valve member 30. It is entirely feasible, on the other hand, to design the latches 166 to pierce through the base ring 32. Inclusion of the coupling ring 162 is suggested, because of its washer-like function in holding the assembly together. However, the latches 166 may be designed to pierce through and securely fasten to stent 160 to the base ring 32 without the use of the coupling ring 162. In this regard, the latches 166 may be configured differently, or more than the number shown may be provided. For example, 4, 6, 8, or more single latch members having a configuration such as shown with a leading sharp point and rearwardly directed barb (much like a fish hook) could fight adequate anchorage through a conventional base ring 32 made of a silicone sponge covered with cloth. Those of skill in the art will understand that there are numerous alternatives available.

The stent 160 in FIGS. 16A and 16B has an outflow end that is preferably sized larger than its inflow end. More particularly, the outflow end is flared so as to receive therein the base ring 32 of the valve member 30. In this way, a larger orifice valve member can be utilized than with a straight tubular stent. The reader is also reminded that at least the flared portion of the stent 160 is desirably provided with a sleeve of Dacron or other such fabric to help prevent paravalvular leaking between the base ring 32 and the surrounding native valve annulus.

Figure 17A:
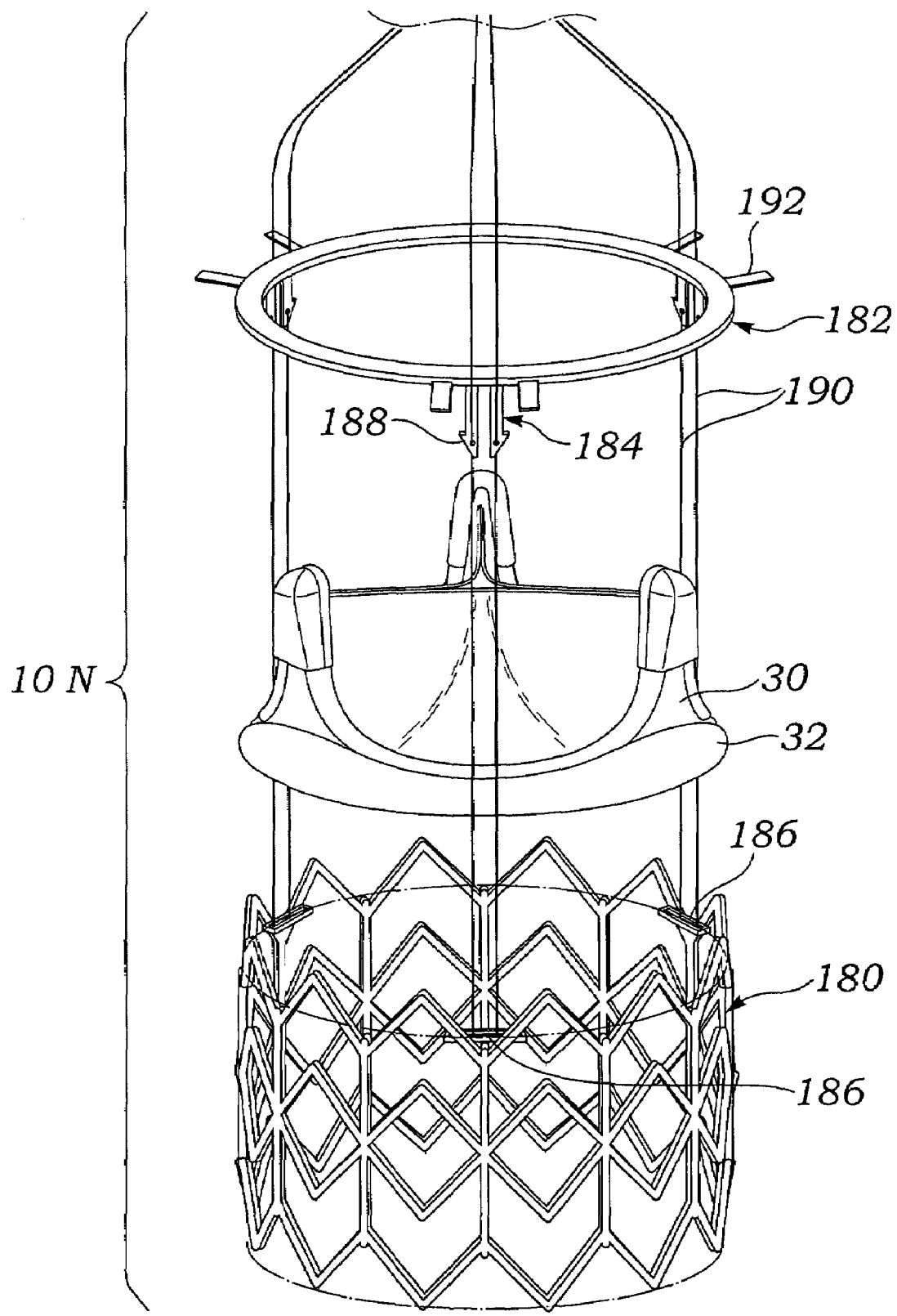
FIGS. 17A and 17B are exploded and assembled perspective views of an alternative prosthetic heart valve wherein a stent has brackets on an outflow end that receive guided locking clips on a locking ring to join the stent to a valve member.
Figure 17B:
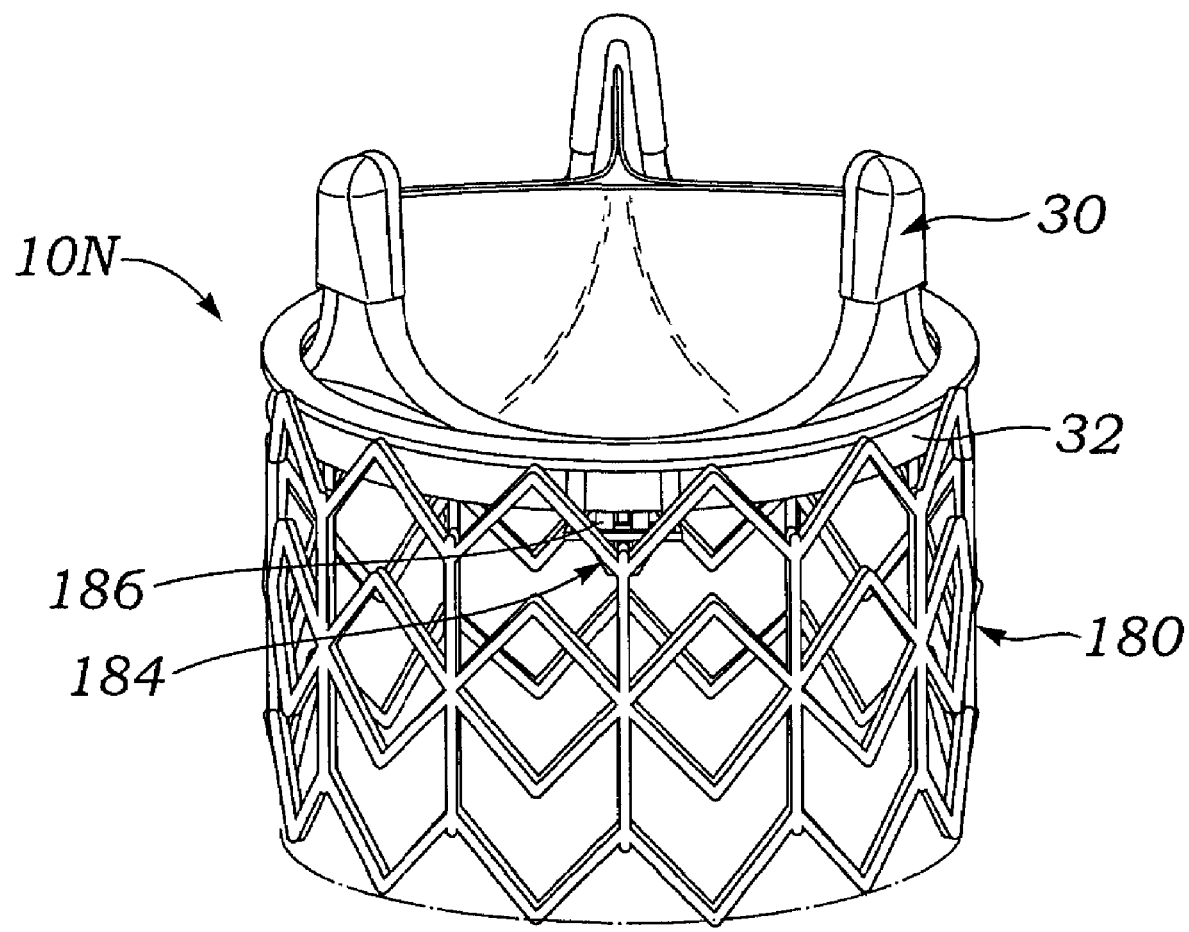

With reference to FIGS. 17A and 17B, yet another two part prosthetic valve 10N is configured for rapid deployment in a heart for replacing a defective native valve. In this version, an expandable anchoring member or stent 180 couples to a valve member 30 through the use of a coupling ring 182 in a manner similar to the last-described embodiment. The coupling ring 182 carries a plurality of latches 184 which mate with brackets 186 provided on the stent 180. In the illustrated embodiment, the latches 184 again comprise a pair of spaced-apart latch members having outwardly directed teeth 188, and the brackets 186 are simply apertures or slots in material loops that extend outward from the stent 180 adjacent its outflow end. Bringing the three components together, the latches 184 extend through the brackets 186 as seen in FIG. 17B. To facilitate proper and rapid passage of the latches 184 through the brackets 186, a plurality of guide filaments 190 loop through the brackets 186 and through holes provided in the latches 184. Simply parachuting the coupling ring 182 down the filaments 190 aims the latches 184 through the brackets 186.

At this stage, it is important to note that any of the fixation rings (i.e., locking ring 112, fixation ring 134, adapter 142, coupling ring 162, or coupling ring 182) described above could be designed to engage the surrounding tissue (annulus) and provide additional protection again paravalvular leakage. For example, a tissue growth factor or fibrin glue or the like may be coated on the exterior of any of these fixation rings for a better seal. Alternatively, the fixation rings might have an outer rim of fabric for encouraging tissue ingrowth. Moreover, the various fixation rings described and the base ring 32 of the valve member 32 may be constructed as a single component. For example, the base ring 32 could be configured to have slots (or any coupling member) in lieu of a separate fixation ring.

Figure 18:
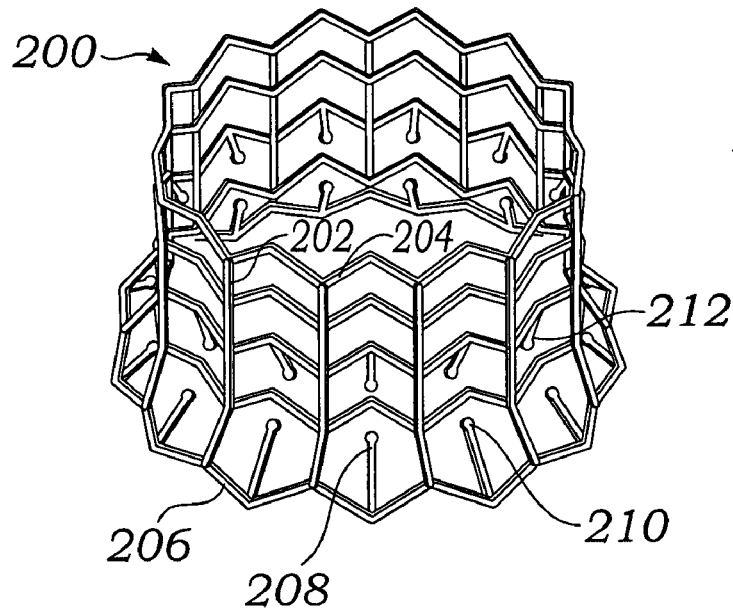
FIG. 18 is a perspective view of an alternative stent for use in a prosthetic heart valve of the present invention.
Figure 19:
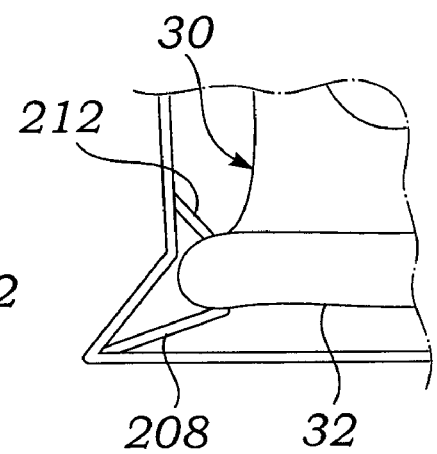
FIG. 19 is a detailed sectional view through an inflow side of a prosthetic heart valve utilizing the stent of FIG. 18 and showing a valve member base ring captured between two sets of prongs.

With reference now to FIG. 18, an alternative expandable anchoring member or stent 200 is illustrated wherein the anchoring member is configured to receive a valve member 30 to form a prosthetic heart valve. As illustrated in FIG. 19, a portion of the valve member is gripped between inwardly extending members located within the stent. More particularly, the stent 200 comprises a plurality of axial struts 202 connected by a number of rows of circumferential crown-shaped struts 204 to form a generally tubular structure. A lower or inflow end of the stent 200 includes a circumferential row of crown-shaped struts 206 that is larger than the others such that the inflow end of the stent flares outward. The upper rows 204 of circumferential struts define valleys (pointing downward) at the axial struts 202 and peaks (pointing upward) midway between each two adjacent axial struts. As seen from FIG. 18, therefore, the spaces defined between adjacent axial struts 202 and adjacent rows of circumferential struts 204 are preferably chevron-shaped, pointed upward. Conversely, the lower circumferential row of struts 206 has upper peaks at the axial struts 202 and lower valleys therebetween, resulting in elongated hexagon-shaped spaces between the lower two circumferential rows of struts.

The stent 200 possesses a plurality of prongs that extend inward therefrom to capture the valve member 30. As seen in FIG. 19, the base ring 32 of the valve member 30 seats on a plurality of lower prongs 208. FIG. 18 shows the lower prongs 208 extending inward from the lower row of struts 206 at the valleys between adjacent axial struts 202. The lower prongs 208 terminate in enlarged heads 210 to prevent damage to the base ring 32. As seen in FIG. 19, the lower prongs 208 project inward farther than the expanded to defined by the upper portion of the stent 200. Additionally, a plurality of upper prongs 212 extend inward from one of the upper rows of circumferential struts 204. In the illustrated embodiment, there are four rows of circumferential struts 204, and the upper prongs 212 project inward from the second lowest row. As seen in FIG. 19, the upper prongs 212 contact the base ring 32 of the valve member 30. In this manner, the valve member 30 is captured between the lower prongs 208 and upper prongs 212.

In the illustrated embodiment, the stent 200 includes twelve axial struts 202, and one of each of the prongs 208, 212 between each adjacent pair of axial struts, resulting in twelve each of the lower and upper prongs. Of course, the number of prongs could be more or less depending on the configuration of the stent 200. Further, there may be more than one prong between adjacent pairs of axial struts 202, or the prongs may be provided only between every other pair. The prongs 208, 212 may be initially flat within the profile of the surrounding struts to prevent interference with an expansion-balloon. After stent deployment they may be bent inward into the angles shown using a tool (not shown). Alternatively, the balloon wall could be relatively thick and able to withstand puncture by the round heads of the prongs 208, 212 such that they are at all times biased inward and automatically assume the angles shown after balloon removal.

To deploy the prosthetic heart valve of FIGS. 18 and 19, the user advances the stent 200 in a collapsed state through the vasculature or a chest port into the target implantation site. Through self-expansion or balloon-expansion, the stent 200 expands into contact with the surrounding valve annulus. The valve member 30 then advances into position adjacent the outflow or upper end of the stent 200. Desirably, the valve member 30 is a conventional non-expandable design, but could also be expandable, in which case it is then expanded prior to assembly with the stent 200.

The outer diameter of the base ring 32 of the valve member 30 is sized approximately the same as the inner diameter of the tubular upper portion of the stent 200. The valve member 30 advances from the outflow end of the stent 200 toward the inflow end until the base ring 32 contacts the circular row of upper prongs 212. The upper prongs 212 are flexible, hinged, or otherwise capable of being displaced outward by the base ring 32 as the valve member 30 passes. Ultimately, the base ring 32 seats on the circular row of relatively non-flexible lower prongs 28 and the valve member 30 cannot be advanced farther. The spacing between the lower prongs 208 and the upper prongs 212 is such that the upper prongs 212 spring inward at the point that the base ring 32 seats on the lower prongs 208. The upper prongs 212 may be formed with blunt heads like the lower prongs 208, or may be straight or even sharp-pointed to pierce the base ring 32 and provided enhanced anchorage. In a preferred embodiment, both the lower prongs 208 and upper prongs 212 possess enlarged, blunt heads such that the base ring 32 is merely trapped between the two sets of prongs.

The design of the stent 200 of FIG. 18 thus enables rapid deployment of a valve member therewithin, as well as positive tactile feedback to the user with valve member 30 is completely installed. Because the base ring 32 is sized closely within the stent 200, good peripheral sealing is provided. To better enhance sealing, a peripheral skirt or layer of graft material may be added on the interior or exterior of the stent 200.

Figure 20:
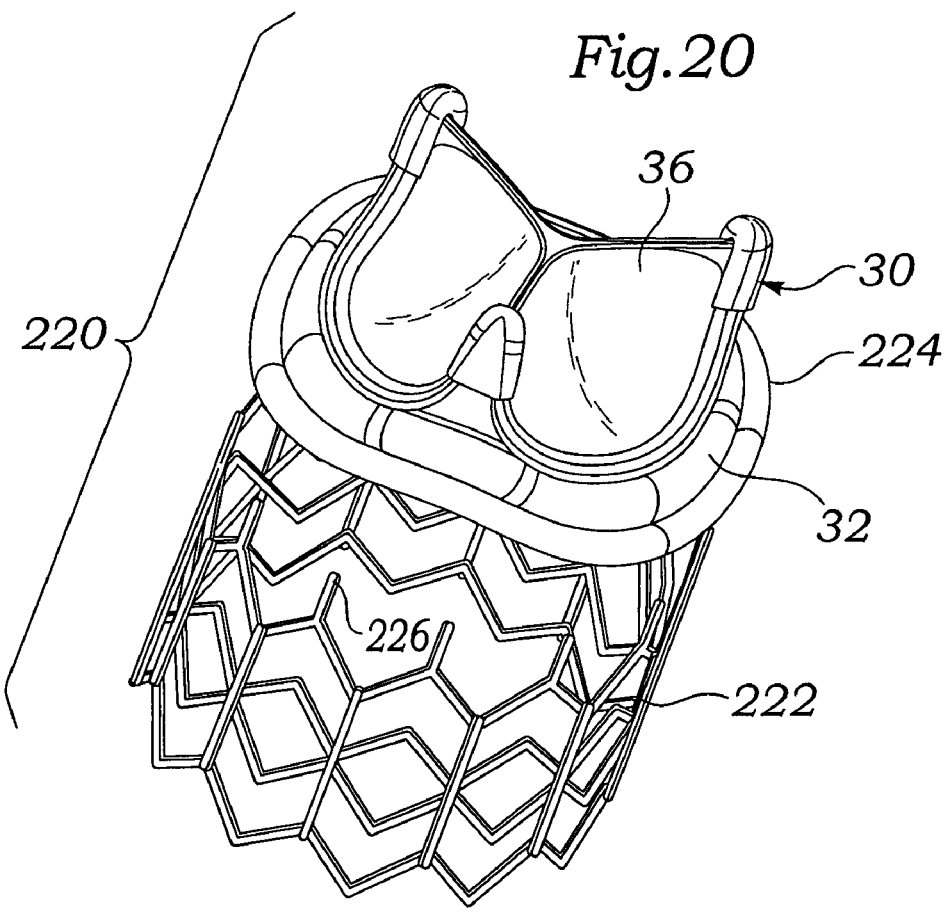
FIG. 20 is a perspective exploded view of a prosthetic heart valve having a tubular stent with upstanding tines and a valve member with an additional adapter ring arranged around a base ring.

With reference to FIG. 20, another embodiment of a prosthetic heart valve 220 comprises a tubular, expandable anchoring member or stent 222, a valve member 30, and an adapter ring 224 for coupling the two components together. The stent 222 and manner of connecting the stent to the valve member 30 is similar to embodiment of FIGS. 3 and 4, and also the embodiment of FIG. 12, in that a plurality of tines 226 project upward from the stent 222. However, instead of the tines 226 piercing or curling around the base ring 32 of the valve member 30, the tines interact with the adapter ring 224. In particular, the adapter ring 224 attaches around the lower periphery of the base ring 32, preferably via a secure stitch line formed during assembly of the valve member 30. The tines 226 pierce or otherwise engage the adapter ring 224 instead of the base ring 32 to couple the valve member 30 to the stent 222. The supplemental adapter ring 224 provides an added margin of safety that helps prevent damage to the valve member 30 by the tines 226. For instance, if the tines 226 are configured to pierce and curl inward, they are farther away from the inner flexible leaflets 36 of the valve member which are susceptible to puncture or tearing.

Figure 21:
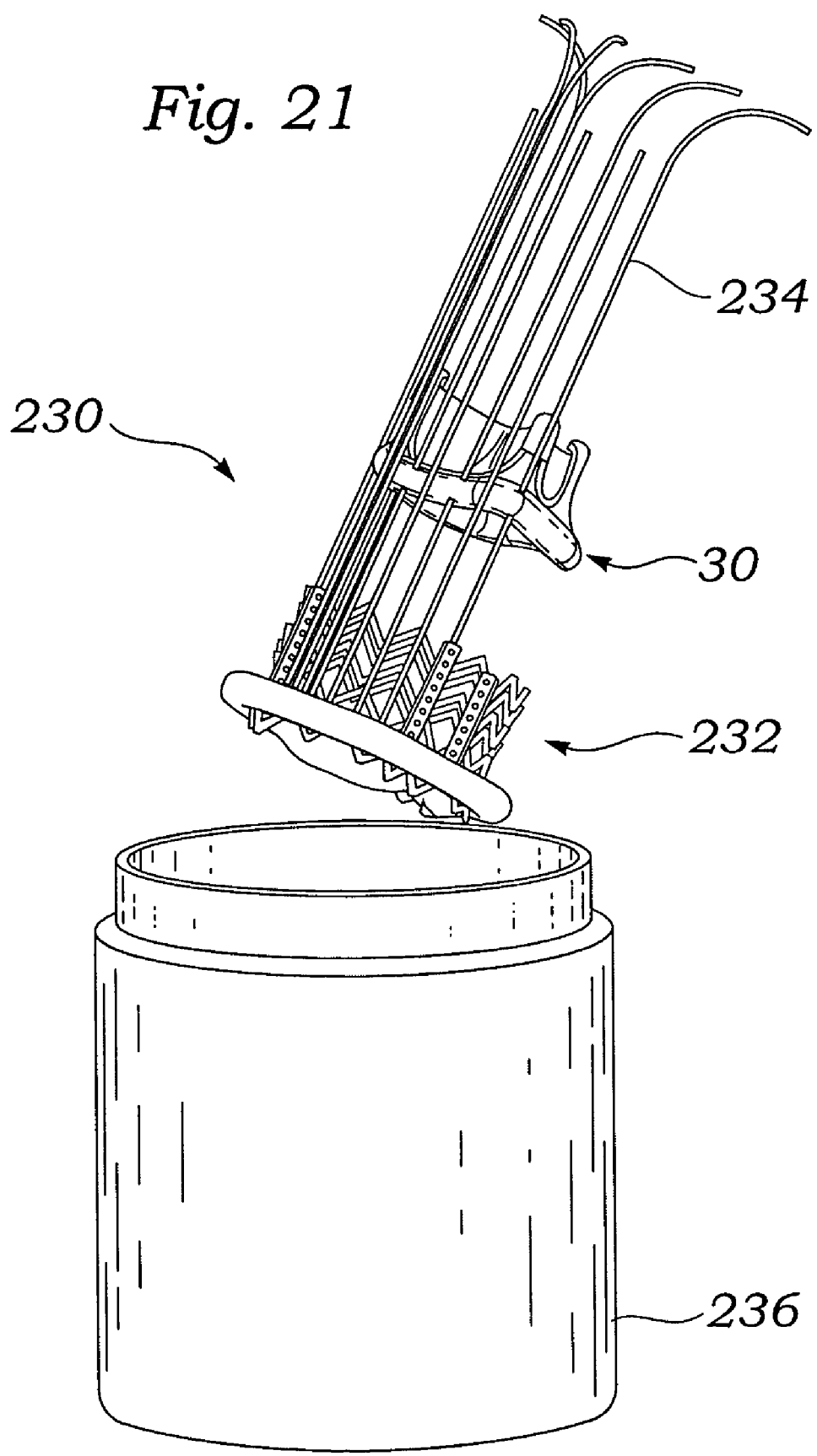
FIG. 21 is an exploded perspective view of an exemplary prosthetic heart valve having an expandable stent and non-expandable valve member connected by an array of parachute sutures being removed from a storage jar.

With reference to FIG. 21, yet another embodiment of a prosthetic heart valve 230 comprises an anchoring member or stent 232 coupled to a valve member 30 via a plurality of sutures 234. The components of the valve 230 are shown exploded above a container or jar 236 used to store the components. In this regard, the entire assembly, including the attachment sutures 234, may be stored together in the jar 236 so as to be ready for deployment. Alternatively, only the stent 232 and valve member 30 may be stored in the jar 236, and the sutures 234 added just prior to deployment but before the actual operation. Still further, the stent 232 can be stored dry in a sterile container, while the valve member 30 having bioprosthetic leaflets may be stored separately in a suitable preservative fluid such as glutaraldehyde. In any event, details of the prosthetic heart valve 230 will be described below with reference to FIGS. 22A through 22C.

Figure 22A:
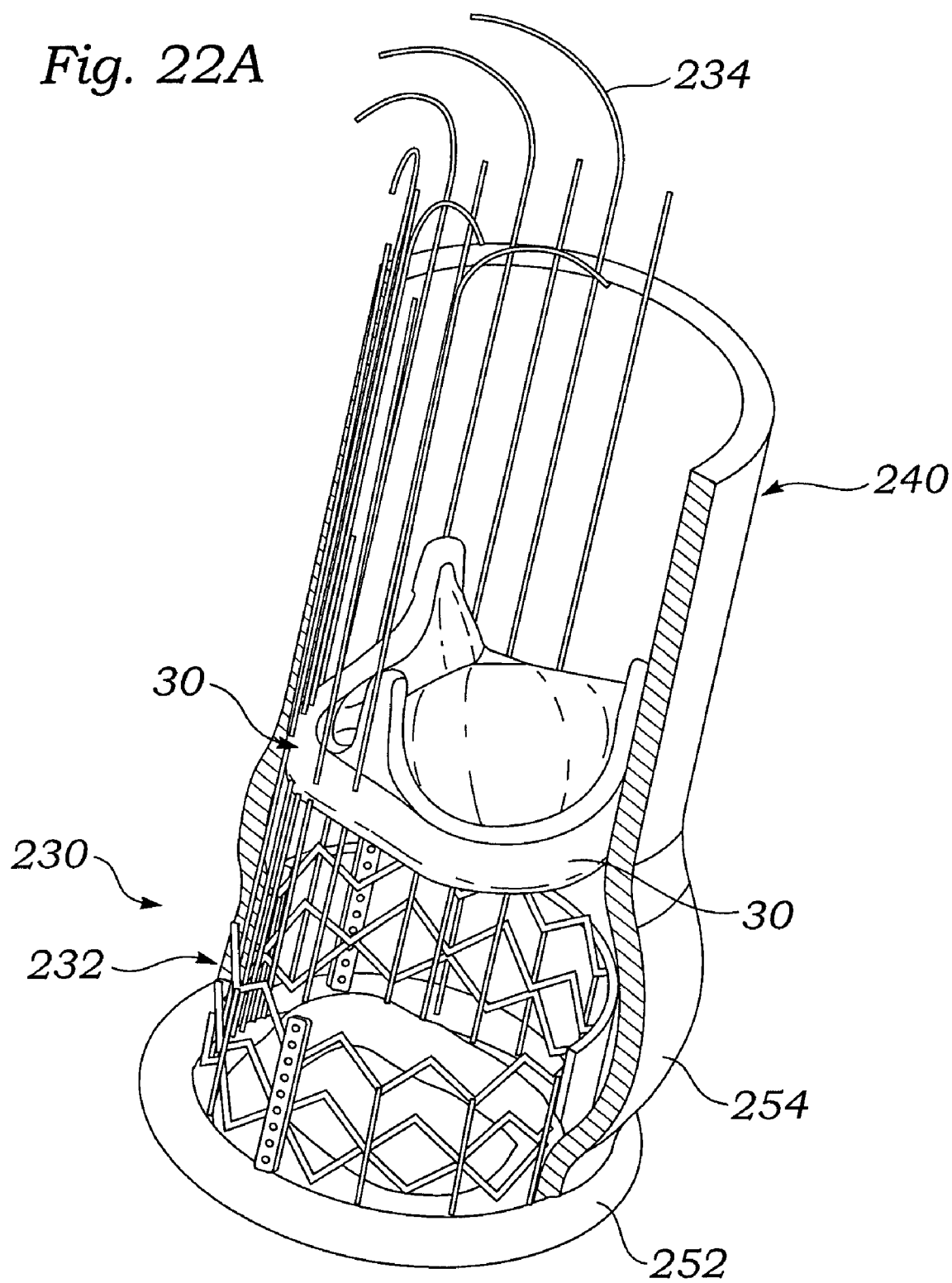
FIGS. 22A-22C are several views of the implantation of the prosthetic heart valve of FIG. 21 assisted by a tubular valve dilator/delivery tube.
Figure 22B:
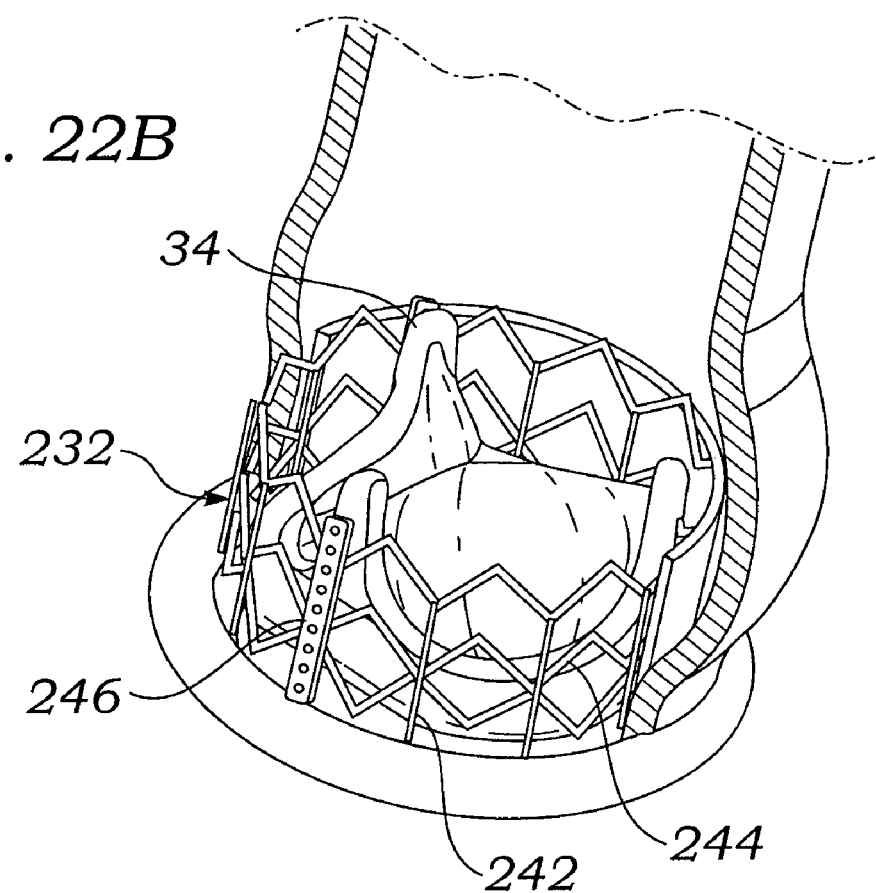
Figure 22C:
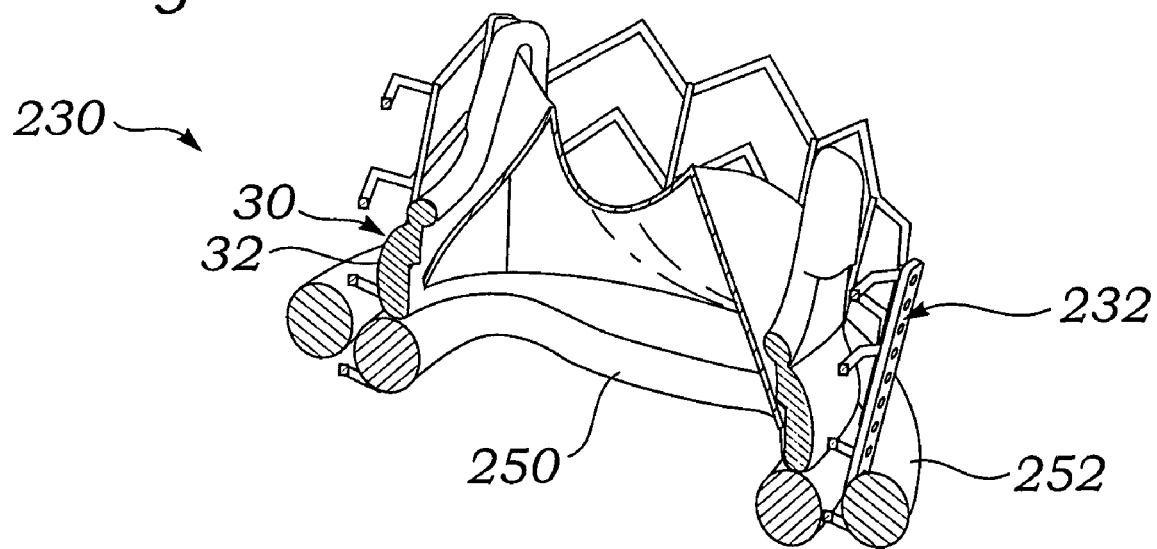

FIGS. 22A through 22C show the components of the prosthetic heart valve 230 in conjunction with a valve dilator/delivery tube 240. The usage of the delivery tube 240 will be described below. The stent 232 comprises an expandable, tubular structure formed of a plurality of axial struts 242 joined by a plurality of angled circumferential struts 244. In this embodiment, there are four rows of circumferential struts 244, the upper two pointing upward, and the lower to pointing downward. The result is a series of both diamond-shaped and chevron-shaped openings. Three axial bars 246 substitute for the more narrow struts 242 at three evenly-spaced positions around the stent 232. As seen in the view of FIG. 22B, the commissures 34 of the valve member 30 align with the axial bars 246.

With reference now to the sectional view of FIG. 22C, the stent 232 additionally comprises an inner fixation ring 250 and an outer sealing ring 252. Both these rings 250, 252 attach to the struts of the stent 232 independently, or to each other through the struts. For example, a series of sutures (not shown) can be used to join the inner ring 250 and outer ring 252 in a relatively continuous circumferential line around the stent 232. These rings are desirably made of suture-permeable, typically compressible material such as silicone rubber, or may be rolled up fabric cuffs. In any event, the inner fixation ring 250 couples to the valve member 30, while the outer sealing ring 252 help prevent leakage around the stent 232.

As seen in FIG. 22A, the attachment sutures 234 extend upward within the stent 232 from the inner fixation ring 250. In this regard, each two strands of the attachment sutures 234 may be defined by looping a single length of suture downward and back upward through the fixation ring 250. The circular array of sutures 234 then passes through corresponding sectors of the base ring 32 of the valve member 30. Again, this can be done at the time of valve assembly, just prior to the valve replacement procedure, or after the stent 232 has been implanted. Those of skill in the art will understand the process of lining up the circular array of attachment sutures 234 into the appropriate locations around the base ring 32 to permit the valve member 32 to parachute down the sutures until it contacts the fixation ring 250.

The entire procedure will now be described in conjunction with use of the valve dilator/delivery tube 240. As mentioned above, the valve replacement procedures described herein are sometimes done without removing the existing native valve. The annulus and valve leaflets are often heavily calcified, and sometimes provide a serious impediment to passage and implant of a replacement valve, even a valve that is initially quite small and balloon expanded. To help widened the orifice in which the prosthetic valve 230 will be implanted, the delivery tube 240 receives all of the valve components therein and acts as a protective sleeve and dilator. In a preferred embodiment, just the sealing ring 252 extends out of the delivery tube 240 at an inflow or leading end thereof.

First, the attachment sutures 234 are preinstalled within the fixation ring 250 and, while maintaining a non-crossing circular array, are passed through the delivery tube 240 to be accessible out the upper end. The sutures 234 are then passed through the appropriate locations within the base ring 32 of the valve member 30. Of course, this can be done during fabrication of the prosthetic heart valve 230, though some structure for maintaining the relative position and orientation of two components is required. In any event, a holder (not shown) attached to the valve member 30 is used to advance the valve member along the array of sutures 234 and within the delivery tube 240, into the approximate position seen in FIG. 22A.

When the patient has been prepared, and an access opening to the target implantation site created, the assembly of the prosthetic heart valve 230 within the delivery tube 240 advances into the body. The leading end comprises the sealing ring 252 and an outwardly bulged portion 254 in the delivery tube 240. For installation in the aortic annulus, the delivery tube 240 advances down the ascending aorta until the stent 232 lines up with the annulus (with the help of radiopaque markers or the like). The outwardly bulged portion 254 in the delivery tube 240 helps open up the calcified annulus. Even if the native valve is resected, sometimes the annulus will shrink a little prior to implant of the valve. The valve dilator/delivery tube 240 thus helps open up the annulus to permit implant of a desired diameter valve. The contour of the bulged portion 254 is relatively smooth, and the material may be Teflon or other such highly lubricated surface so that the tube easily slips through the annulus. A slight back-and-forth movement may be required to fully open the annulus.

At this stage, the delivery tube 250 retracts relative to the stent 232, through the use of a pusher (not shown) for example, such that the stent 232 may fully expand into the annulus. The stent 232 may be self-expanding and thus be only partially expanded within the delivery tube 240. When the delivery tube 240 is removed, the stent 232 springs outward into firm engagement with the annulus. Alternatively, a balloon (not shown) may be used to accomplish the final expansion of the stent 232, which configuration would require a catheter passing through the center of the valve leaflets 34. If the stent 232 is balloon expandable, consideration must be taken of the continual attachment of the valve to the guide sutures 234. On the other hand, if the stent 232 is self-expanding, then typically an auxiliary sheath would be provided to hold the stent in the contracted condition.

When the user is satisfied that the stent 232 is properly positioned, the valve member 30 is advanced using the aforementioned holder (not shown). As the valve member 30 advances, care is taken to ensure that the attachment sutures 234 remain untangled and taut. Ultimately, the valve member 30 seats on the fixation ring 250 as seen in FIGS. 22B and 22C. At this point, the user ties and severs the attachment sutures 234 in a conventional manner. The provision of the sealing ring 252 directly adjacent and surrounding the fixation ring 250 greatly enhances the ability of the prosthetic valve 230 to resist paravalvular leaking.

In one advantageous feature, preferred embodiments of the component based prosthetic valves described herein may be used with existing technology. For example, certain stent embodiments may be configured for attachment to sewing rings provided on existing prosthetic valves. In other cases, valve member require only small variations in order to be used with the component based system. Not only will this contribute to a lower price for the final valve, but also learned familiarity to the system for surgeons who might be hesitant to adopt a completely new system.

It will be appreciated by those skilled in the art that embodiments of the present invention provide important new devices and methods wherein a valve may be securely anchored to a body lumen in a quick and efficient manner. Embodiments of the present invention provide a means for implanting a prosthetic valve in a surgical procedure without requiring the surgeon to suture the valve to the tissue. Accordingly, the surgical procedure time is substantially decreased. Furthermore, in addition to providing an anchoring member for the valve, the stent may be used to maintain the native valve in a dilated condition. As a result, it is not necessary for the surgeon to remove the native leaflets, thereby further reducing the procedure time.

It will also be appreciated that the present invention provides an improved system wherein a valve member may be replaced in a more quick and efficient manner. More particularly, it is not necessary to cut any sutures in order to remove the valve. Rather, the valve member may be disconnected from the stent (or other support structure) and a new valve member may be connected in its place. This is an important advantage when using biological tissue valves or other valves having limited design lives. Still further, it will be appreciated that the devices and methods of the present invention may be configured for use in a minimally invasive approach (e.g., through a small incision between the ribs) or in a percutaneous procedure while still remaining within the scope of the invention.

While the invention has been described in its preferred embodiments, it is to be understood that the words which have been used are words of description and not of limitation. Therefore, changes may be made within the appended claims without departing from the true scope of the invention.

What is claimed is:

1. A surgical method of implanting a prosthetic heart valve in a patient, comprising:

providing a two-stage prosthetic heart valve comprising an expandable anchoring member and a valve member, the anchoring member being sized to contact a heart valve annulus in an expanded state and the valve member being configured to connect to the anchoring member, the anchoring member having opposed ends and the valve member having a plurality of commissure posts axially extending to tips and supporting flexible leaflets therebetween;

preparing the patient for surgery by placing him/her on cardiopulmonary bypass;

creating a direct access pathway to the heart valve annulus that permits direct naked eye vision of the heart valve annulus;

delivering and expanding the anchoring member to contact the heart valve annulus; and delivering and connecting the valve member at a first end of the anchoring member such that the commissure post tips are located outside of the anchoring member by attaching members between the first end of the anchoring member and over the tips of the commissure posts of the valve member.

2. The method of claim 1, wherein the step of creating a direct access pathway comprises performing open-heart surgery.

3. The method of claim 1, wherein the step of delivering and expanding the anchoring member comprises balloon-expanding the anchoring member.

4. The method of claim 1, wherein the valve member is expandable, and the step of delivering and connecting the valve member comprises delivering the valve member in a compressed state and expanding it prior to connecting it to the anchoring member.

5. The method of claim 1, wherein the valve member and the anchoring member are further provided with mating connectors, and the step of delivering and connecting the valve member to the anchoring member comprises axially displacing the valve member toward the anchoring member so that the mating connectors engage.

6. The method of claim 1, wherein the anchoring member comprises a stent having an outflow end larger than an inflow end thereof, and wherein the valve member comprises a non-expandable valve member having a base ring on an inflow end thereof sized to fit within the outflow end of the stent, wherein the step of delivering and connecting the valve member to the anchoring member comprises positioning the valve member within the outflow end of the stent.

7. The method of claim 1, wherein the members attaching the first end of the anchoring member to the commissure posts of the valve member include bendable connectors on an outflow end thereof, and the method includes causing the connectors to bend inward and engage the tips of the commissure posts.

8. The method claim 7, wherein the step of causing the connectors to bend inward comprises actuating a bending tool that is removed from the implantation site thereafter.

9. A surgical method of implanting a two-stage prosthetic heart valve in a patient, comprising:

providing an expandable anchoring member sized to contact a heart valve annulus in an expanded state, the anchoring member having opposed ends;

delivering and attaching the anchoring member to the heart valve annulus;

providing a non-expandable valve member having a plurality of commissure posts axially extending to tips and supporting flexible leaflets therebetween; and delivering and connecting the valve member at a first end of the anchoring member such that the commissure post tips are located outside of the anchoring member by attaching members between the first end of the anchoring member and over the tips of the commissure posts.

10. The method of claim 9, wherein the valve member and the anchoring member are provided with mating connectors, and the step of delivering and connecting the valve member to the anchoring member comprises axially displacing the valve member toward the anchoring member so that the mating connectors engage.

11. The method of claim 9, wherein the anchoring member comprises a stent having an outflow end larger than an inflow end thereof, and wherein the valve member comprises a base ring on an inflow end thereof sized to fit within the outflow end of the stent, wherein the step of delivering and connecting the valve member to the anchoring member comprises positioning the valve member within the outflow end of the stent.

12. The method of claim 9, wherein the members attaching the first end of the anchoring member to the commissure posts of the valve member include bendable connectors on an outflow end thereof, and the method includes causing the connectors to bend inward and engage the tips of the commissure posts.

13. The method claim 12, wherein the step of causing the connectors to bend inward comprises actuating a bending tool that is removed from the implantation site thereafter.

14. The method of claim 9, wherein the valve member includes a base ring on an inflow end thereof, and the method further includes providing an adapter sized to surround the valve member and seat on the base ring, the step of delivering and connecting the valve member comprises coupling the adapter to the anchoring member.

15. The method of claim 14, wherein the adapter includes a plurality of discrete connectors, and the anchoring member comprises a tubular structure having a plurality of mating connectors spaced around a peripheral outflow end thereof, the step of coupling the adapter to the anchoring member comprises displacing the adapter toward the anchoring member to engage the mating connectors thereon.

16. The heart valve of claim 14, wherein the adapter further includes a plurality of connectors adapted to engage and couple the adapter directly to the base ring, and the method includes causing the connectors to engage the base ring.

17. The method of claim 1, wherein the members attaching the first end of the anchoring member to the commissure posts of the valve member are configured to change shape from a first configuration to a second configuration that wraps over the tips of the commissure posts.

18. The method of claim 17, wherein the members are formed of a malleable material, and the step of connecting the prosthetic heart valve to the anchoring member includes bending the members from the first configuration to the second configuration.

19. The method of claim 17, wherein the members are hinged and can be pivoted from the first configuration to the second configuration, and the step of connecting the prosthetic heart valve to the anchoring member includes pivoting the members from the first configuration to the second configuration.

20. The method of claim 17, wherein the members are formed of a shape memory material that curls from the first configuration to the second configuration upon being implanted in the body.

21. The method of claim 9, wherein the members attaching the first end of the anchoring member to the commissure posts of the valve member are hinged and can be pivoted from the first configuration to the second configuration, and the step of connecting the prosthetic heart valve to the anchoring member includes pivoting the members from the first configuration to the second configuration.

22. The method of claim 9, wherein the members attaching the first end of the anchoring member to the commissure posts of the valve member are formed of a shape memory material that curls from the first configuration to the second configuration upon being implanted in the body.

* * * * *